US012575735B2

(12) United States Patent
Dacosta et al.

(10) Patent No.: US 12,575,735 B2
(45) Date of Patent: Mar. 17, 2026

(54) DEVICES, SYSTEMS, AND METHODS FOR TUMOR VISUALIZATION AND REMOVAL

(71) Applicant: SBI ALAPHARMA CANADA INC., Toronto (CA)

(72) Inventors: Ralph S. Dacosta, Etobicoke (CA); Kathryn Ottolino-Perry, Toronto (CA); Christopher Gibson, Toronto (CA); Nayana Thalanki Anantha, Scarborough (CA); Simon Treadwell, Toronto (CA); Todd Daynes, Aurora (CA); Todd Meaney, Thornhill (CA); Garrett Vermey, Toronto (CA); Carl Annis, Oakville (CA)

(73) Assignees: SBI ALAPHARMA CANADA INC., Toronto (CA); University Health Network, Toronto (CA)

( * ) Notice: Subject to any disclaimer, the term of this patent is extended or adjusted under 35 U.S.C. 154(b) by 1059 days.

(21) Appl. No.: 17/423,609

(22) PCT Filed: Jan. 17, 2020

(86) PCT No.: PCT/IB2020/050383
§ 371 (c)(1),
(2) Date: Jul. 16, 2021

(87) PCT Pub. No.: WO2020/148724
PCT Pub. Date: Jul. 23, 2020

(65) Prior Publication Data
US 2022/0104706 A1 Apr. 7, 2022

Related U.S. Application Data

(60) Provisional application No. 62/857,155, filed on Jun. 4, 2019, provisional application No. 62/793,764, filed on Jan. 17, 2019.

(51) Int. Cl.
*A61B 5/00* (2006.01)
*A61B 46/10* (2016.01)
(Continued)

(52) U.S. Cl.
CPC .......... *A61B 5/0071* (2013.01); *A61B 5/0091* (2013.01); *A61B 46/10* (2016.02);
(Continued)

(58) Field of Classification Search
CPC ................ A61B 5/0071; A61B 5/0091; A61B 2562/0242; A61B 1/043; A61B 2090/309
See application file for complete search history.

(56) References Cited

U.S. PATENT DOCUMENTS

| | | | |
|---|---|---|---|
| 3,945,371 A | 3/1976 | Adelman | |
| D414,867 S | 10/1999 | Moriwaki et al. | |

(Continued)

FOREIGN PATENT DOCUMENTS

| | | |
|---|---|---|
| AU | 2014373656 | 7/2016 |
| CA | 208795 | 3/2022 |

(Continued)

OTHER PUBLICATIONS

Supplementary Partial European Search report dated Sep. 20, 2022 in related EP Application No. 20740856.8, 12 pages.
(Continued)

*Primary Examiner* — Gerald Johnson
(74) *Attorney, Agent, or Firm* — Jones Robb, PLLC

(57) ABSTRACT

An imaging device includes a body having a first end portion configured to be held in a user's hand and a second end portion configured to direct light onto a surgical margin. The device includes at least one excitation light source configured to excite autofluorescence emissions of tissue cells and fluorescence emissions of induced porphyrins in tissue cells of the surgical margin. A white light source is configured to
(Continued)

illuminate the surgical margin during white light imaging of the surgical margin. The device includes an imaging sensor, a first optical filter configured to permit passage of auto-fluorescence emissions of tissue cells and fluorescence emissions of the induced porphyrins in tissue cells to the imaging sensor, and a second optical filter configured to permit passage of white light emissions of tissues in the surgical margin to the imaging sensor. Systems and methods relate to imaging devices.

95 Claims, 16 Drawing Sheets

(51) Int. Cl.
*A61K 49/00* (2006.01)
*A61B 90/00* (2016.01)

(52) U.S. Cl.
CPC ...... *A61K 49/0021* (2013.01); *A61K 49/0034* (2013.01); *A61B 2090/3941* (2016.02); *A61B 2560/0425* (2013.01); *A61B 2560/0443* (2013.01); *A61B 2562/0242* (2013.01)

(56) References Cited

U.S. PATENT DOCUMENTS

| | | | |
|---|---|---|---|
| 5,971,918 A | 10/1999 | Zanger | |
| 6,190,309 B1 | 2/2001 | Ooshima et al. | |
| 6,393,315 B1 | 5/2002 | Aprahamian et al. | |
| 6,571,119 B2 | 5/2003 | Hayashi | |
| 6,601,997 B2 | 8/2003 | Ngo | |
| D480,478 S | 10/2003 | Leonard et al. | |
| 6,678,398 B2 | 1/2004 | Wolters et al. | |
| 6,889,075 B2 | 5/2005 | Marchitto et al. | |
| D515,214 S | 2/2006 | Jackson, III et al. | |
| D542,820 S | 5/2007 | Depay | |
| D569,378 S | 5/2008 | Wanamaker | |
| D585,554 S | 1/2009 | Suzuki | |
| D605,759 S | 12/2009 | Cuevas et al. | |
| D610,178 S | 2/2010 | Adolfsson et al. | |
| 7,846,091 B2 | 12/2010 | Fulghum | |
| D636,424 S | 4/2011 | Lin | |
| D658,298 S | 4/2012 | Prpa | |
| D677,793 S | 3/2013 | Prpa | |
| 8,620,410 B2 | 12/2013 | Frangioni | |
| D698,937 S | 2/2014 | Laverack et al. | |
| D701,606 S | 3/2014 | Ohmukai | |
| D703,331 S | 4/2014 | Kitayama | |
| D703,333 S | 4/2014 | Saeki | |
| D724,234 S | 3/2015 | Hagege | |
| 9,042,967 B2 | 5/2015 | Dacosta et al. | |
| D733,595 S | 7/2015 | Hoshino | |
| D747,391 S | 1/2016 | Sakai | |
| D748,808 S | 2/2016 | Matsumura et al. | |
| D750,260 S | 2/2016 | Sauer | |
| D753,308 S | 4/2016 | Marinkovich et al. | |
| D755,062 S | 5/2016 | Yarden | |
| 9,326,666 B2 | 5/2016 | Frangioni | |
| 9,340,490 B2 | 5/2016 | Okura et al. | |
| 9,451,882 B2 | 9/2016 | Nie et al. | |
| D787,684 S | 5/2017 | Vezina | |
| 9,743,836 B2 | 8/2017 | Tsubouchi et al. | |
| D802,777 S | 11/2017 | Burachynsky et al. | |
| D810,293 S | 2/2018 | Peel | |
| D820,987 S | 6/2018 | Tam et al. | |
| D822,747 S | 7/2018 | Van Deusen et al. | |
| D822,748 S | 7/2018 | Van Deusen et al. | |
| D827,014 S | 8/2018 | Sakai | |
| D835,271 S | 12/2018 | Myers et al. | |
| D849,105 S | 5/2019 | Hogstedt et al. | |
| D850,628 S | 6/2019 | De Hoog et al. | |
| D859,498 S | 9/2019 | Lin | |
| D861,176 S | 9/2019 | Yoon et al. | |
| D861,764 S | 10/2019 | Zhao | |
| D862,697 S | 10/2019 | Kenworthy et al. | |
| 10,438,356 B2 | 10/2019 | Dacosta | |
| D865,836 S | 11/2019 | Puusaari | |
| D865,845 S | 11/2019 | Sakai | |
| D866,764 S | 11/2019 | Pukall | |
| D868,867 S | 12/2019 | Jean et al. | |
| D873,890 S | 1/2020 | Fidler | |
| D884,175 S | 5/2020 | Aubailly et al. | |
| D907,097 S | 1/2021 | Suurmeijer et al. | |
| D908,161 S | 1/2021 | Dacosta et al. | |
| D908,881 S | 1/2021 | Dacosta et al. | |
| D910,105 S | 2/2021 | Lin | |
| D910,182 S | 2/2021 | Dacosta et al. | |
| D913,354 S | 3/2021 | Marzette, Jr. et al. | |
| D914,220 S | 3/2021 | Nelson et al. | |
| D916,294 S | 4/2021 | Murray et al. | |
| D919,093 S | 5/2021 | Takahashi | |
| D919,690 S | 5/2021 | Suurmeijer et al. | |
| D921,736 S | 6/2021 | Yin | |
| D921,899 S | 6/2021 | Suarez et al. | |
| D922,469 S | 6/2021 | Sjogren et al. | |
| D924,306 S | 7/2021 | Melnicoff | |
| D930,845 S | 9/2021 | Schmidt et al. | |
| D936,827 S | 11/2021 | Wang | |
| D952,023 S | 5/2022 | Dacosta et al. | |
| D958,991 S | 7/2022 | Dacosta et al. | |
| D959,666 S | 8/2022 | Dacosta et al. | |
| D967,420 S | 10/2022 | Sun | |
| 12,245,840 B2 | 3/2025 | Dacosta et al. | |
| 2001/0049473 A1 | 12/2001 | Hayashi | |
| 2003/0191368 A1 | 10/2003 | Wang et al. | |
| 2004/0225222 A1 | 11/2004 | Zeng et al. | |
| 2005/0029437 A1 | 2/2005 | Hasegawa et al. | |
| 2005/0234526 A1* | 10/2005 | Gilhuly ............... A61B 5/0077 |
| | | | 600/102 |
| 2005/0288594 A1 | 12/2005 | Lewkowicz et al. | |
| 2006/0004292 A1 | 1/2006 | Beylin | |
| 2006/0241493 A1 | 10/2006 | Feldman et al. | |
| 2008/0059070 A1 | 3/2008 | Boyden et al. | |
| 2008/0188758 A1 | 8/2008 | Campbell et al. | |
| 2009/0137908 A1* | 5/2009 | Patwardhan ........... A61B 5/444 |
| | | | 600/476 |
| 2010/0084563 A1 | 4/2010 | Ohno | |
| 2010/0145146 A1 | 6/2010 | Melder | |
| 2010/0145419 A1 | 6/2010 | Fraval | |
| 2010/0292580 A1 | 11/2010 | Gilhuly et al. | |
| 2011/0117025 A1* | 5/2011 | Dacosta ............... A61B 5/0059 |
| | | | 435/5 |
| 2011/0152692 A1 | 6/2011 | Nie et al. | |
| 2011/0275900 A1 | 11/2011 | Gilhuly et al. | |
| 2011/0305422 A1* | 12/2011 | Thompson ........... G02B 6/4471 |
| | | | 385/94 |
| 2012/0016230 A1* | 1/2012 | Kishima .............. A61B 1/0646 |
| | | | 600/425 |
| 2012/0056996 A1 | 3/2012 | Sander et al. | |
| 2012/0101390 A1 | 4/2012 | Iftimia et al. | |
| 2012/0165627 A1 | 6/2012 | Yamamoto | |
| 2012/0323124 A1* | 12/2012 | Corbett, III .......... A61B 8/4472 |
| | | | 600/459 |
| 2013/0216482 A1 | 8/2013 | Kwon et al. | |
| 2013/0338479 A1 | 12/2013 | Pogue et al. | |
| 2014/0180116 A1 | 6/2014 | Lindekugel et al. | |
| 2014/0275772 A1 | 9/2014 | Chuda | |
| 2014/0276102 A1 | 9/2014 | Lee et al. | |
| 2014/0276103 A1 | 9/2014 | Lee et al. | |
| 2015/0030542 A1 | 1/2015 | Singhal | |
| 2015/0038837 A1 | 2/2015 | Inoue et al. | |
| 2015/0150460 A1 | 6/2015 | Krishnaswamy et al. | |
| 2015/0182118 A1 | 7/2015 | Bradbury et al. | |
| 2015/0182196 A1 | 7/2015 | Ninomiya et al. | |
| 2015/0198797 A1 | 7/2015 | Andre et al. | |
| 2015/0230696 A1 | 8/2015 | Tuch et al. | |
| 2016/0045114 A1 | 2/2016 | Dacosta et al. | |
| 2016/0062103 A1* | 3/2016 | Yang ........................ A61B 1/07 |
| | | | 250/552 |
| 2016/0206202 A1 | 7/2016 | Frangioni | |
| 2016/0287194 A1 | 10/2016 | Nariyuki et al. | |
| 2016/0287211 A1 | 10/2016 | DaCosta et al. | |

(56) References Cited

U.S. PATENT DOCUMENTS

| | | | |
|---|---|---|---|
| 2017/0000320 A1* | 1/2017 | Wilson | A61B 90/50 |
| 2017/0085855 A1 | 3/2017 | Roberts et al. | |
| 2017/0143418 A1 | 5/2017 | Lee | |
| 2017/0156597 A1 | 6/2017 | Whitehead | |
| 2017/0209050 A1* | 7/2017 | Fengler | H04N 23/74 |
| 2017/0235118 A1 | 8/2017 | Kuster et al. | |
| 2017/0236281 A1* | 8/2017 | Dacosta | G06T 7/0016 |
| | | | 382/128 |
| 2017/0280969 A1 | 10/2017 | Levy et al. | |
| 2017/0290515 A1 | 10/2017 | Butte et al. | |
| 2017/0325698 A1 | 11/2017 | Allec et al. | |
| 2018/0014764 A1 | 1/2018 | Bechtel et al. | |
| 2018/0070806 A1 | 3/2018 | Matsuo et al. | |
| 2018/0098741 A1 | 4/2018 | Lu et al. | |
| 2018/0133320 A1* | 5/2018 | Babic | C07F 9/091 |
| 2018/0206739 A1 | 7/2018 | Forero Cortes et al. | |
| 2018/0218508 A1 | 8/2018 | Lee et al. | |
| 2018/0234603 A1* | 8/2018 | Moore | G03B 15/05 |
| 2018/0242848 A1 | 8/2018 | Dacosta et al. | |
| 2018/0252909 A1 | 9/2018 | Regensburger et al. | |
| 2018/0276814 A1 | 9/2018 | Frangioni | |
| 2018/0279864 A1 | 10/2018 | Frangioni | |
| 2018/0310829 A1* | 11/2018 | Frangioni | A61B 34/20 |
| 2018/0325377 A1 | 11/2018 | Dacosta et al. | |
| 2018/0369603 A1 | 12/2018 | Gjersvik et al. | |
| 2019/0079011 A1 | 3/2019 | Frangioni | |
| 2019/0159663 A1* | 5/2019 | Krstajic | A61B 1/0669 |
| 2019/0209000 A1 | 7/2019 | Treado et al. | |
| 2019/0216325 A1 | 7/2019 | Ouyang | |
| 2020/0128166 A1 | 4/2020 | Fukumoto | |
| 2020/0188033 A1 | 6/2020 | Komp et al. | |
| 2020/0359884 A1* | 11/2020 | Swisher | G02B 27/017 |
| 2021/0228300 A1 | 7/2021 | DaCosta et al. | |
| 2021/0378584 A1 | 12/2021 | Takahashi et al. | |
| 2022/0007942 A1 | 1/2022 | Stith et al. | |
| 2022/0061671 A1 | 3/2022 | Dacosta et al. | |
| 2022/0071559 A1 | 3/2022 | Jones et al. | |
| 2022/0072294 A1* | 3/2022 | Locke | A61M 39/10 |
| 2022/0248944 A1 | 8/2022 | Dacosta et al. | |

FOREIGN PATENT DOCUMENTS

| | | |
|---|---|---|
| CN | 101208037 | 6/2008 |
| CN | 103654699 | 3/2014 |
| CN | 104271046 | 1/2015 |
| CN | 104394754 | 3/2015 |
| CN | 105212880 | 1/2016 |
| CN | 106714670 | 5/2017 |
| CN | 106983495 | 7/2017 |
| CN | 107093171 | 8/2017 |
| CN | 304554755 | 3/2018 |
| CN | 108139329 | 6/2018 |
| CN | 108289723 | 7/2018 |
| CN | 109044277 | 12/2018 |
| CN | 306141139 | 10/2020 |
| CN | 307182522 | 9/2022 |
| CN | 307545922 | 9/2022 |
| CN | 307713119 | 12/2022 |
| EA | 006624763-0002 | 7/2019 |
| EP | 1880660 | 1/2008 |
| EP | 2502551 | 9/2012 |
| EP | 3372143 | 9/2018 |
| EP | 4284131 | 11/2023 |
| JP | H08224208 | 9/1996 |
| JP | H09-000488 | 1/1997 |
| JP | H10151104 | 6/1998 |
| JP | 2003190091 | 7/2003 |
| JP | 2004305367 | 11/2004 |
| JP | 2005124776 | 5/2005 |
| JP | 2006509573 | 3/2006 |
| JP | 2006166940 | 6/2006 |
| JP | 2006340796 | 12/2006 |
| JP | 2007244746 | 9/2007 |
| JP | 2009045148 | 3/2009 |
| JP | 2009066121 | 4/2009 |
| JP | 2011521237 | 7/2011 |
| JP | 2012157383 | 8/2012 |
| JP | 2012532689 | 12/2012 |
| JP | 2013514156 | 4/2013 |
| JP | 2013123647 | 6/2013 |
| JP | 2013531538 | 8/2013 |
| JP | 2015139613 | 8/2015 |
| JP | 2016030214 | 3/2016 |
| JP | 2016-520339 | 7/2016 |
| JP | 2017060778 | 3/2017 |
| JP | 2017524935 | 8/2017 |
| JP | 2017192501 | 10/2017 |
| JP | 2024-160225 | 11/2024 |
| JP | 7648525 | 3/2025 |
| KR | 10-1503891 | 3/2015 |
| KR | 300827516.0000 | 11/2015 |
| KR | 10-2016-0065258 | 6/2016 |
| WO | 2010080611 | 7/2010 |
| WO | 2013184830 | 12/2013 |
| WO | 2015154094 | 10/2015 |
| WO | 2016011534 | 1/2016 |
| WO | 2016063949 | 4/2016 |
| WO | 2017079844 | 5/2017 |
| WO | 2017082242 | 5/2017 |
| WO | 2017096137 | 6/2017 |
| WO | 2018145193 | 8/2018 |
| WO | 2019148268 | 8/2019 |
| WO | 2019213737 | 11/2019 |
| WO | 2020148724 | 7/2020 |
| WO | 2020148725 | 7/2020 |
| WO | 2020148726 | 7/2020 |

OTHER PUBLICATIONS

Supplementary European Search report dated Sep. 20, 2022 in related EP Application No. 20741034.1, 27 pages.
Supplementary European Search report dated Sep. 26, 2022 in related EP Application No. 20741678.5, 9 pages.
Office Action dated Sep. 16, 2022 in related CA Application No. 3,127,036.
Notice of Allowance dated Sep. 27, 2022 in related JP Application No. 2022-003401.
Office Action dated Oct. 6, 2022 in related CA Application No. 3,127,048.
Office Action dated Sep. 27, 2022 in related JP Application No. 2022-019073.
European Search report dated Jan. 5, 2023 in related EP Application No. 20740856. 8.
First Examination report dated Feb. 3, 2023 in related IN App No. 202117030136.
Notice of Allowance in Design U.S. Appl. No. 29/762,417, dated Jan. 13, 2022, 13 pages.
Notice of Allowance in Design U.S. Appl. No. 29/767,502 dated Mar. 11, 2022, 5 pages.
Notice of Allowance in U.S. Appl. No. 29/767,874 dated Mar. 21, 2022.
U.S. Appl. No. 29/842,182, filed Jun. 10, 2022.
U.S. Appl. No. 29/842,512, filed Jun. 14, 2022.
Office Action dated Jun. 21, 2022 in related Brazilian Application No. BR 302022000890-7.
International Search Report and Written Opinion from International Application No. PCT/IB2020/050383, dated Apr. 23, 2020.
International Search Report and Written Opinion from International Application No. PCT/IB2020/050384, dated Apr. 22, 2020.
International Search Report and Written Opinion from International Application No. PCT/IB2020/050385, dated Apr. 8, 2020.
First Examination report dated Jun. 30, 2022 in related IN App No. 202017037681.
U.S. Appl. No. 62/793,842, filed Jan. 17, 2019.
U.S. Appl. No. 62/793,846, filed Jan. 17, 2019.
U.S. Appl. No. 62/857,183, filed Jun. 4, 2019.
Design U.S. Appl. No. 29/676,901, filed Jan. 15, 2019.
Design U.S. Appl. No. 29/677,152, filed Jan. 17, 2019.

(56)            References Cited

OTHER PUBLICATIONS

International Search Report and Written Opinion from International Patent Application No. PCT/CA2019/000015, dated Jun. 4, 2019.
"Fluorescent chemical probes for accurate tumor diagnosis and targeting therapy", 2017, Gao et al. https://www.researchgate.net/publication/315469453 Fluorescent chemical probes for accurate tumor diagnosis and targeting therapy.
"Current concepts and future perspectives on surgical optical imaging in cancer",2010, Ntziachristos et al., https://www.sniedigitallibrary.orMoumals/Jounial-of-Biomedical-Onticstvolume-15issue-61066024/Current-concepts-and-future-perspectives-on-surgical-optical-imaging-in/10.1117/1.3523364.full7SSO=I.
Notice of Allowance in Design U.S. Appl. No. 29/677,154, dated Apr. 1, 2020.
Notice of Allowance in Design U.S. Appl. No. 29/677,152, dated Apr. 1, 2020.
Ex Parte Quayle Action in Design U.S. Appl. No. 29/676,901, dated Mar. 5, 2020.
Notice of Allowance in Design U.S. Appl. No. 29/676,901, dated Jun. 4, 2020.
International Patent Application No. PCT/IB2020/050384, dated Jan. 17, 2020.
International Patent Application No. PCT/IB2020/050383, dated Jan. 17, 2020.
International Patent Application No. PCT/IB2020/050385, dated Jan. 17, 2020.
Notice of Allowance in Design U.S. Appl. No. 29/677,152, dated Sep. 22, 2020.
Notice of Allowance in Design U.S. Appl. No. 29/676,901, dated Sep. 18, 2020.
Ex Parte Quayle Action in Design U.S. Appl. No. 29/677,152, dated Dec. 20, 2019.
Design U.S. Appl. No. 29/762,417, filed Dec. 16, 2020.
Design U.S. Appl. No. 29/767,502, filed Jan. 22, 2021.
U.S. Appl. No. 17/423,447, filed Jul. 15, 2021.
Design U.S. Appl. No. 29/804,808, filed Aug. 23, 2021.
U.S. Appl. No. 17/423,576, filed Jul. 16, 2021.
Office Action dated Aug. 17, 2021 in related U.S. Appl. No. 29/762,417, 9 pages.
European Search Report for EP Application No. EP19746801 dated Sep. 13, 2021, 2 pages.
"Nagaya et al Fluorescence-Guided Surgery", Frontiers in Oncology, vol. 7, Dec. 22, 2017, 16 pp.
Ex Parte Quayle Action dated Nov. 30, 2021 for U.S. Appl. No. 29/767,502, 8 pages.
Ex Parte Quayle Action dated Nov. 30, 2021 for U.S. Appl. No. 29/767,874, 5 pages.
Office Action dated Apr. 4, 2023 received in related JP Application No. 2020-541946.
Written Opinion dated Apr. 21, 2023 in related Application No. 11202107275Q.
Office Action dated Jul. 13, 2023 in related CA Application No. 3,127,048.
Decision Of Rejection dated Jul. 25, 2023 in related JP Application No. 2020-541946.
Office Action dated Jul. 14, 2023 in related CA Application No. 3,127,036.
Notification of the First Rectification dated Jul. 5, 2023 in related CN Application No. 2022300861326.
Office Action dated Jun. 20, 2023 received in related JP Application No. 2023-003578.
Examination Report dated Aug. 10, 2023 in related CA Application No. 210515.
Office Action dated Oct. 3, 2023 received in related U.S. Appl. No. 29/842,512, 8 pages.
Baycare, Lumicell, Inc. Selects BayCare for Pivotal Breast Cancer Trial, Published on: Oct. 9, 2020, Baycare.org, Retrieved from Internet: https://baycare.org/newsroom/2020/october/lumicell-inc-selects-baycare-for-pivotal-breast-cancer-clinical-trial (Year: 2020).

Office Action dated Oct. 3, 2023 received in related JP Application No. 2021-541493.
Office Action dated Oct. 3, 2023 received in related JP Application No. 2021-541474.
Notice of Allowance dated Oct. 13, 2023 in related U.S. Appl. No. 29/842,182, 9 pages.
Advanced Endoscopy Devices, Inc, Introducing the Multi-Disciplinary Use of the AED ENDOPRO-CAM® Elite, Uploaded on: Mar. 11, 2020, YouTube, Retrieved from Internet: https://www.youtube.com/watch?v=rnxtMz2JhFg (Year: 2020).
SBI ALAPharma, The Eagle V1.2 Imaging System, Downloaded on: Aug. 22, 2023, sbi-alapharmacanada.ca, Retrieved from Internet: https://www.sbi-alapharmacanada.ca/technology (Year: 2023).
Office Action dated Nov. 7, 2023 received in related JP Application No. 2021-541486.
Office Action dated Sep. 27, 2023 received in related CN Application No. 2020800191924.
Office Action dated Nov. 4, 2023 received in related CA Application No. 225,390.
Office Action dated Sep. 28, 2023 received in CN Application No. 2019800233835.
Examination report dated Nov. 30, 2023 received in AU Application No. 2019215811.
European Search Report dated Jan. 12, 2024 received in EP Application No. 23188747.2.
Office Action dated Jan. 17, 2024 in related CN Application No. 2020800184047.
Office Action dated Jan. 24, 2024 in related U.S. Appl. No. 16/966,293, 18 pp.
Office Action dated Oct. 12, 2023 in related CN Application No. 2020800219686.
Office Action dated Jan. 11, 2024 in related CN Application No. 2022300861326.
Notice of Allowance dated Feb. 5, 2024 in related U.S. Appl. No. 29/842,512.
Office Action dated Feb. 20, 2024 in related U.S. Appl. No. 17/423,447, 25 pp.
Office Action dated Feb. 22, 2024 in related U.S. Appl. No. 17/423,576, 26 pp.
Office Action dated Jan. 26, 2024 in related MX Application No. MX/f/2022/000423.
Office Action dated Mar. 27, 2024 in related CA Application No. 3,127,039.
Office Action dated Mar. 28, 2024 in related CA Application No. 3,090,190.
Office Action dated Apr. 3, 2024 in related CN Application No. 2019800233835.
Office Action dated Jul. 4, 2024 received in related CN Application No. 2020800191924.
Office Action dated Apr. 22, 2024 received in related Application No. MX/a/2020/008159.
Office Action dated May 23, 2024 in related MX Application No. MX/f/2022/000423.
Notice of Grant dated Jun. 11, 2024 Issued in related JP Application No. 2021-541486.
Notice of Allowance dated May 27, 2024 in related MX/f/2024/000967.
Notice of Allowance dated May 27, 2024 in related MX/f/2024/000968.
Office Action dated Jul. 16, 2024 received in related JP Application No. 2021-541493.
Office Action dated Jul. 16, 2024 received in related JP Application No. 2021-541474.
Notice of Allowance dated Jun. 11, 2024 in related CA Application No. 3,127,048.
Office Action dated Jun. 28, 2024 received in related CN Application No. 2019800233835.
Office Action dated Sep. 2, 2024 received in related EP Application No. 19746801.0.
Office Action dated Sep. 3, 2024 received in related JP Application No. 2023-199730.
Office Action dated Jul. 25, 2024 in related MX Application No. MX/a/2021/008504.

(56)     References Cited

OTHER PUBLICATIONS

Examination Report dated Sep. 6, 2024 received in related AU Application No. 2020209518.
Examination Report dated Sep. 5, 2024 received in related AU Application No. 2020209276.
Office Action dated Aug. 6, 2024 received in related CN Application No. 2020800219686.
Examination Report dated Sep. 27, 2024 received in related AU Application No. 2020208843.
Notice of Allowance dated Oct. 30, 2024 received in related U.S. Appl. No. 17/423,447, 7 pp.
Office Action dated Oct. 16, 2024 received in related CN Application No. 2019800233835.
Final Office Action dated Nov. 1, 2024 received in related U.S. Appl. No. 17/423,576, 22 pages.
Final Office Action dated Nov. 7, 2024 received in related U.S. Appl. No. 16/966,293, 21 pp.
Office Action dated Nov. 14, 2024 received in related Korean Application No. 10-2021-7026033.
Corrected Notice of Allowability dated Nov. 27, 2024 received in related U.S. Appl. No. 17/423,447.
Office Action dated Oct. 17, 2024 received in related CN Application No. 2020800184047.
Office Action dated Nov. 20, 2024 received in related MX Application No. MX/a/2020/008159.
Notice of Issuance dated Nov. 22, 2024 in related CN Application No. 2024301422414.
Office Action dated Oct. 24, 2024 in related Canadian Application No. 3,127,036.
Corrected Notice of Allowability dated Jan. 8, 2025 received in related U.S. Appl. No. 17/423,447.
Notice of Allowance dated Jan. 20, 2025 received in related MX Application No. MX/a/2021/008504.
Notice of Grant dated Feb. 4, 2025 in related Japanese Application No. 2021-541474.

Office Action dated Feb. 4, 2025 received in related Japanese Application No. 2021-541493.
Office Action dated Feb. 12, 2025 received in JP Application No. 2020-541946.
Office Action dated Jan. 1, 2025 received in related JP Application No. 2020800219686.
Notice of Allowance dated Feb. 24, 2025 received in related MX Application No. MX/a/2020/008159.
Office Action dated Feb. 12, 2025 in related CN Application No. 2020800191924.
Application and Drawings filed Mar. 10, 2025 in U.S. Appl. No. 19/075,323.
Office Action dated Mar. 11, 2025 in related JP Application No. 2023-199730.
Masafumi Oyama et al., "Application of PDD to renal cell carcinoma", Japanese Journal of Endourology, vol. 24, Japanese Society of Endourology and Robotics, 2011, p. 23-28, URL:https://www.j stage.j st.go.jp/ article/j sejj e/24/1/24_23 /_pdf.
Office Action dated Mar. 14, 2025 in related Canadian Application No. 3,090, 190.
Office Action dated Aug. 13, 2025 received in related U.S. Appl. No. 16/966,293, 25 pages.
Office Action dated Jul. 18, 2025 in related CA Application No. 3,127,039.
Office Action dated Jul. 23, 2025 received in related KR Application No. 10-2021-7026039.
Office Action dated Jul. 29, 2025 received in related JP Application No. 2024-110804.
Office Action dated Aug. 26, 2025 received in related BR Application No. BR1120200157570.
Office Action dated Sep. 2, 2025 received in related BR Application No. BR 112021013992-3.
Office Action dated Sep. 11, 2025 in related EP Application No. 20741678.5.

* cited by examiner

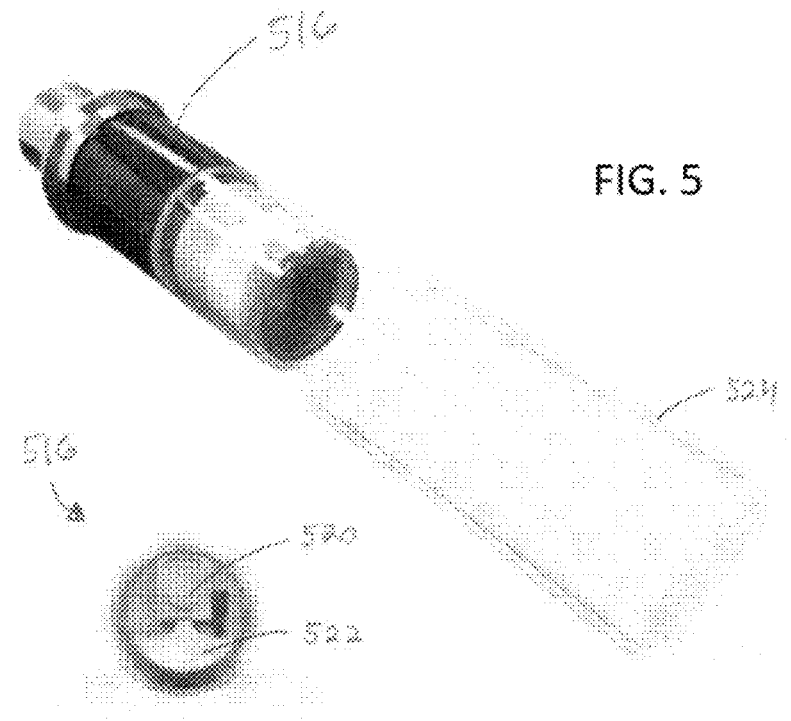
FIG. 5
FIG. 6
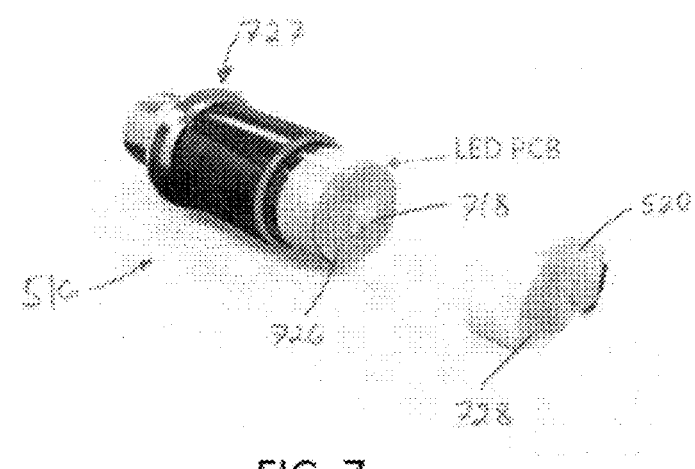
FIG. 7

DEVICES, SYSTEMS, AND METHODS FOR TUMOR VISUALIZATION AND REMOVAL

CROSS-REFERENCE TO RELATED APPLICATIONS

This application is a U.S. national stage application under 35 U.S.C. § 371(c) of International Application No. PCT/IB2020/050383, filed Jan. 17, 2020, which claims priority to U.S. Provisional Application No. 62/793,764 (filed Jan. 17, 2019), entitled "DEVICES, SYSTEMS, AND METHODS FOR TUMOR VISUALIZATION AND REMOVAL," and U.S. Provisional Application No. 62/857,155 (filed Jun. 4, 2019), entitled "DEVICES, SYSTEMS, AND METHODS FOR TUMOR VISUALIZATION AND REMOVAL," the entire contents of each of which are incorporated by reference herein.

TECHNICAL FIELD

The present disclosure relates to devices, systems, and methods for tumor visualization and removal. The disclosed devices, systems, and methods may also be used to stage tumors and to assess surgical margins such as tissue margins on excised tumors and margins on tissue beds/surgical beds from which a tumor and/or tissue has been removed. The disclosed devices, systems, and methods may also be used to identify one or more of residual cancer cells, precancerous cells, and satellite lesions and to provide guidance for removal and/or treatment of the same.

INTRODUCTION

Surgery is one of the oldest types of cancer therapy and is an effective treatment for many types of cancer. Oncology surgery may take different forms, dependent upon the goals of the surgery. For example, oncology surgery may include biopsies to diagnose or determine a type or stage of cancer, tumor removal to remove some or all of a tumor or cancerous tissue, exploratory surgery to locate or identify a tumor or cancerous tissue, debulking surgery to reduce the size of or remove as much of a tumor as possible without adversely affecting other body structures, and palliative surgery to address conditions caused by a tumor such as pain or pressure on body organs.

In surgeries in which the goal is to remove the tumor(s) or cancerous tissue, surgeons often face uncertainty in determining if all cancer has been removed. The surgical bed, or tissue bed, from which a tumor is removed, may contain residual cancer cells, i.e., cancer cells that remain in the surgical margin of the area from which the tumor is removed. If these residual cancer cells remain in the body, the likelihood of recurrence and metastasis increases. Often, the suspected presence of the residual cancer cells, based on examination of surgical margins of the excised tissue during pathological analysis of the tumor, leads to a secondary surgery to remove additional tissue from the surgical margin.

For example, breast cancer, the most prevalent cancer in women, is commonly treated by breast conservation surgery (BCS), e.g., a lumpectomy, which removes the tumor while leaving as much healthy breast tissue as possible. Treatment efficacy of BCS depends on the complete removal of malignant tissue while leaving enough healthy breast tissue to ensure adequate breast reconstruction, which may be poor if too much breast tissue is removed. Visualizing tumor margins under standard white light (WL) operating room conditions is challenging due to low tumor-to-normal tissue contrast, resulting in reoperation (i.e., secondary surgery) in approximately 23% of patients with early stage invasive breast cancer and 36% of patients with ductal carcinoma in situ. Re-excision is associated with a greater risk of recurrence, poorer patient outcomes including reduced breast cosmesis and increased healthcare costs. Positive surgical margins (i.e., margins containing cancerous cells) following BCS are also associated with decreased disease specific survival.

Current best practice in BCS involves palpation and/or specimen radiography and rarely, intraoperative histopathology to guide resection. Specimen radiography evaluates excised tissue margins using x-ray images and intraoperative histopathology (touch-prep or frozen) evaluates small samples of specimen tissue for cancer cells, both of which are limited by the time delay they cause (~20 min) and inaccurate co-localization of a positive margin on the excised tissue to the surgical bed. Thus, there is an urgent clinical need for a real-time, intraoperative imaging technology to assess excised specimen and surgical bed margins and to provide guidance for removal of one or more of residual cancer cells, precancerous cells, and satellite lesions.

SUMMARY

The present disclosure may solve one or more of the above-mentioned problems and/or may demonstrate one or more of the above-mentioned desirable features. Other features and/or advantages may become apparent from the description that follows.

In accordance with one aspect of the present disclosure, an imaging device includes a body having a first end portion configured to be held in a user's hand and a second end portion configured to direct light onto a surgical margin. The device includes at least one excitation light source configured to excite autofluorescence emissions of tissue cells and fluorescence emissions of induced porphyrins in tissue cells of the surgical margin. A white light source is configured to illuminate the surgical margin during white light imaging of the surgical margin. The device includes an imaging sensor, a first optical filter configured to filter optical signals emitted by the surgical margin responsive to illumination with excitation light and permit passage of autofluorescence emissions of tissue cells and fluorescence emissions of the induced porphyrins in tissue cells to the imaging sensor, and a second optical filter configured to filter optical signals emitted by the surgical margin responsive to illumination with white light and permit passage of white light emissions of tissues in the surgical margin to the imaging sensor.

In accordance with another aspect of the present disclosure, an imaging device includes a body having a first end portion configured to be held in a user's hand and a second end portion configured to direct light onto a surgical margin, a first excitation light source configured to emit excitation light having a first wavelength, and a second excitation light source configured to emit excitation light having a second wavelength. An imaging sensor is configured to detect emissions of the surgical margin. A first optical filter is configured to filter optical signals emitted by the surgical margin responsive to illumination of the surgical margin with the first excitation light. The first filter is configured to permit optical signals having a wavelength corresponding to a first characteristic of the surgical margin to pass through the filter to the imaging sensor. A second optical filter is configured to filter optical signals emitted by the surgical margin responsive to illumination of the surgical margin with the first excitation light, the second filter configured to permit optical signals having a wavelength corresponding to a second characteristic of the surgical margin, different from the first characteristic, to pass through the filter to the imaging sensor.

In accordance with yet another aspect of the present disclosure, a method of imaging tissue at a surgical margin comprises illuminating the tissue at the surgical margin with a first excitation light source configured to emit excitation light having a first wavelength, receiving optical signals emitted by the tissue at the surgical margin through a first optical filter in an imaging device, illuminating the tissue at the surgical margin with a second excitation light source configured to emit excitation light having a second wavelength, and receiving optical signals emitted by the tissue at the surgical margin through a second optical filter in the imaging device.

BRIEF DESCRIPTION OF THE DRAWINGS

The present disclosure can be understood from the following detailed description either alone or together with the accompanying drawings. The drawings are included to provide a further understanding and are incorporated in and constitute a part of this specification. The drawings illustrate one or more exemplary embodiments of the present disclosure and together with the description serve to explain various principles and operations.

FIG. 5 is a perspective view of a distal end portion of a handheld imaging device including a drape according to the present disclosure.

FIG. 6 is an end view of a distal end portion of a handheld imaging device according to the disclosure.

FIG. 7 is an exploded view of the distal end portion of FIG. 6.

DESCRIPTION OF VARIOUS EXEMPLARY EMBODIMENTS

Figure 1:
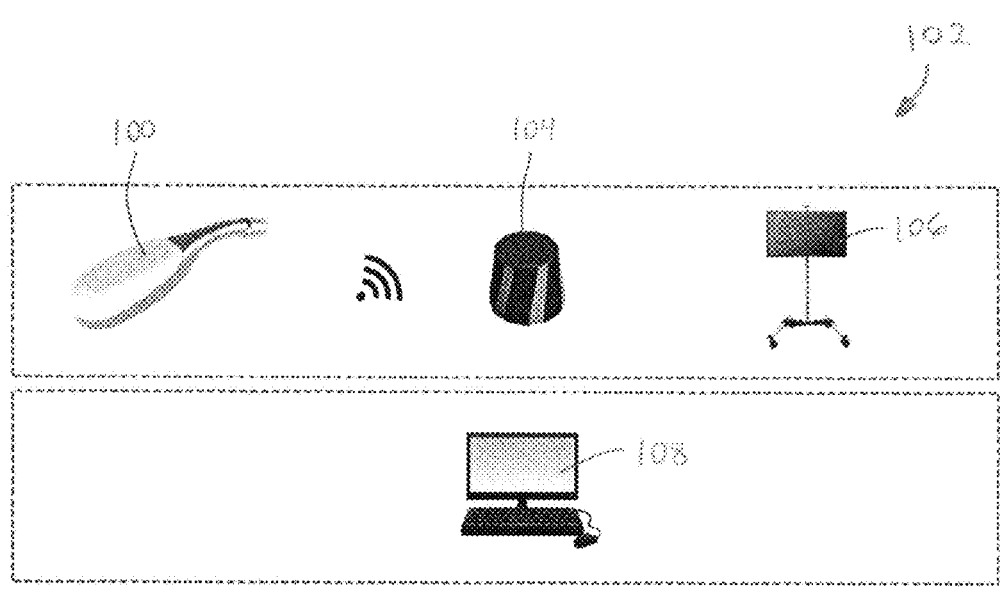
FIG. 1 is a diagram of a system for tumor visualization according to the present disclosure.

Existing surgical margin assessment technologies focus on the excised sample to determine whether surgical margins include residual cancer cells. These technologies are limited by their inability to accurately spatially co-localize a positive margin detected on the excised sample to the surgical bed, a limitation the present disclosure overcomes by directly imaging the surgical cavity.

Other non-targeted techniques for reducing re-excisions include studies which combine untargeted margin shaving with standard of care BCS. While this technique may reduce the overall number of re-excisions, the approach includes several potential drawbacks. For example, larger resections are associated with poorer cosmetic outcomes and the untargeted removal of additional tissues is contradictory to the intention of BCS. In addition, the end result of using such a technique appears to be in conflict with the recently updated ASTRO/SSO guidelines, which defined positive margins as 'tumor at ink' and found no additional benefit of wider margins. Moran M S, Schnitt S J, Giuliano A E, Harris J R, Khan S A, Horton J et al., "Society of Surgical Oncology-American Society for Radiation Oncology consensus guideline on margins for breast-conserving surgery with whole-breast irradiation in stages I and II invasive breast cancer," Ann Surg Oncol. 2014. 21(3): 704-716. A recent retrospective study found no significant difference in re-excisions following cavity shaving relative to standard BCS. Pata G, Bartoli M, Bianchi A, Pasini M, Roncali S, Ragni F., "Additional Cavity Shaving at the Time of Breast-Conserving Surgery Enhances Accuracy of Margin Status Examination," Ann Surg Oncol. 2016. 23(9): 2802-2808. Should margin shaving ultimately be found effective, FL-guided surgery may be used to refine the process by adding the ability to target specific areas in a surgical margin for shaving, thus turning an untargeted approach, which indiscriminately removes additional tissue, into a targeted approach that is more in line with the intent of BCS.

The present application discloses devices, systems, and methods for fluorescent-based visualization of tumors, including in vivo and in vitro visualization and/or assessment of tumors, multifocal disease, and surgical margins, and intraoperative guidance for removal of residual tumor, satellite lesions, precancerous cells, and/or cancer cells in surgical margins. In certain embodiments, the devices disclosed herein are handheld and are configured to be at least partially positioned within a surgical cavity. In other embodiments, the devices are portable, without wired connections. However, it is within the scope of the present disclosure that the devices may be larger than a handheld device, and instead may include a handheld component. In such embodiments, it is contemplated that the handheld component may be connected to a larger device housing or system by a wired connection.

Also disclosed are methods for intraoperative, in-vivo imaging using the device and/or system. The imaging device may be multispectral. It is also contemplated that the device may be hyperspectral. In addition to providing information regarding the type of cells contained within a surgical margin, the disclosed devices and systems also provide information regarding location (i.e., anatomical context) of cells contained within a surgical margin. In addition, methods of providing guidance for intraoperative treatment of surgical margins using the device are disclosed, for example, fluorescence-based image guidance of resection of a surgical margin. The devices, systems, and methods disclosed herein may be used on subjects that include humans and animals.

In accordance with one aspect of the present disclosure, some disclosed methods combine use of the disclosed devices and/or systems with administration of a non-activated, non-targeted compound configured to induce porphyrin in tumor/cancer cells, precancer cells, and/or satellite lesions. For example, the subject may be given a diagnostic dose (i.e., not a therapeutic dose) of a compound (imaging/contrast agent) such as the pro-drug aminolevulinic acid (ALA). As understood by those of ordinary skill in the art, dosages of ALA less than 60 mg/kg are generally considered diagnostic while dosages greater than 60 mg/kg are generally considered therapeutic. As disclosed herein, the diagnostic dosage of ALA may be greater than 0 mg/kg and less than 60 kg/mg, between about 10 mg/kg and about 50 mg/kg, between about 20 mg/kg and 40 mg/kg, and may be administered to the subject in a dosage of 5 mg/kg, 10 mg/kg, 15 kg/mg, 20 mg/kg, 25 mg/kg, 30 mg/kg, 35 mg/kg, 40 mg/kg, 45 mg/kg, 50 mg/kg, or 55 mg/kg. The ALA may be administered orally, intravenously, via aerosol, via immersion, via lavage, and/or topically. Although a diagnostic dosage is contemplated for visualization of the residual cancer cells, precancer cells, and satellite lesions, it is within the scope of the present disclosure to use the disclosed devices, systems, and methods to provide guidance during treatment and/or removal of these cells and/or lesions. In such a case, the surgeon's preferred method of treatment may vary based on the preferences of the individual surgeon. Such treatments may include, for example, photodynamic therapy (PDT). In cases where PDT or other light-based therapies are contemplated as a possibility, administration of a higher dosage of ALA, i.e., a therapeutic dosage rather than a diagnostic dosage, may be desirable. In these cases, the subject may be prescribed a dosage of ALA higher than 60 mg/kg.

The ALA induces porphyrin formation (protoporphyrin IX (PpIX)) in tumor/cancer cells which when excited by the appropriate excitation light, results in a red fluorescence emission from cells containing the PpIX, which enhances the red-to-green fluorescence contrast between the tumor/cancer tissue cells and normal tissue cells (e.g., collagen) imaged with the device. ALA is non-fluorescent by itself, but PpIX is fluorescent at around 630 nm, 680 nm, and 710 nm, with the 630 nm emission being the strongest. Alternatively, the endogenous fluorescent difference between tumor/cancer cells or precancer cells and normal/healthy cells may be used without an imaging/contrast agent.

In exemplary embodiments, the non-activated, non-targeted compound configured to induce porphyrin in tumor/cancer cells, precancer cells, and/or satellite lesions is administered to a subject between about 15 minutes and about 6 hours before surgery, about 1 hour and about 5 hours before surgery, between about 2 hours and about 4 hours before surgery, or between about 2.5 hours and about 3.5 hours before surgery. These exemplary time frames allow sufficient time for the ALA to be converted to porphyrins in tumor/cancer cells, precancer cells, and/or satellite lesions. The ALA or other suitable compound may be administered orally, intravenously, via aerosol, via immersion, via lavage, and/or topically.

In cases where the administration of the compound is outside of the desired or preferred time frame, it is possible that PpIX may be further induced (or induced for the first time if the compound was not administered prior to surgery) by, for example, applying the compound via an aerosol composition, i.e., spraying it into the surgical cavity or onto the excised tissue (before or after sectioning for examination). Additionally or alternatively, the compound may be administered in a liquid form, for example as a lavage of the surgical cavity. Additionally or alternatively, with respect to the removed specimen, PpIX may be induced in the excised specimen if it is immersed in the liquid compound, such as liquid ALA, almost immediately after excision. The sooner the excised tissue is immersed, the better the chance that PpIX or additional PpIX will be induced in the excised tissue.

During surgery, the tumor, such as a primary, palpable, or index tumor, is removed by the surgeon, if possible. The handheld, fluorescence-based imaging device is then used to identify, locate, and guide treatment of any residual cancer cells, precancer cells, and/or satellite lesions in the surgical bed from which the tumor has been removed. The device may also be used to examine the excised tumor/tissue specimen to determine if any tumor/cancer cells and/or precancer cells are present on the outer margin of the excised specimen. The presence of such cells may indicate a positive margin, to be considered by the surgeon in determining whether further resection of the surgical bed is to be performed. The location of any tumor/cancer cells identified on the outer margin of the excised specimen can be used to identify a corresponding location on the surgical bed, which may be targeted for further resection and/or treatment. This may be particularly useful in situations in which visualization of the surgical bed itself does not identify any residual tumor/cancer cells, precancer cells, or satellite lesions. In addition, the handheld, fluorescence-based imaging device can be used to guide the surgical resection of the primary tumor itself, and then to look for residual cancer cells, precancer cells, and/or satellite lesions in the surgical bed from which the tumor has been removed as discussed above.

Figure 2:
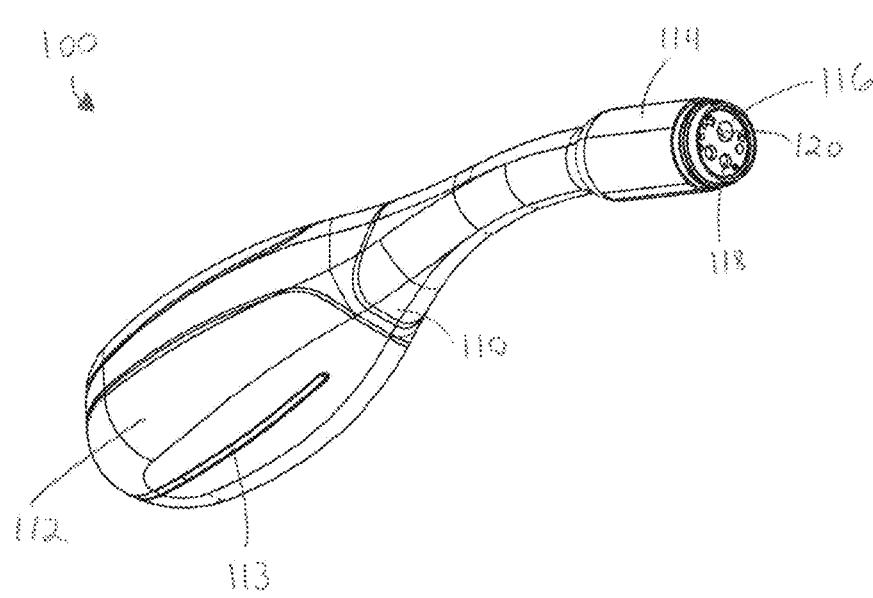
FIG. 2 is a perspective view of a handheld imaging device for visualization of tumor/cancer cells according to an embodiment of the present disclosure.
Figure 3:
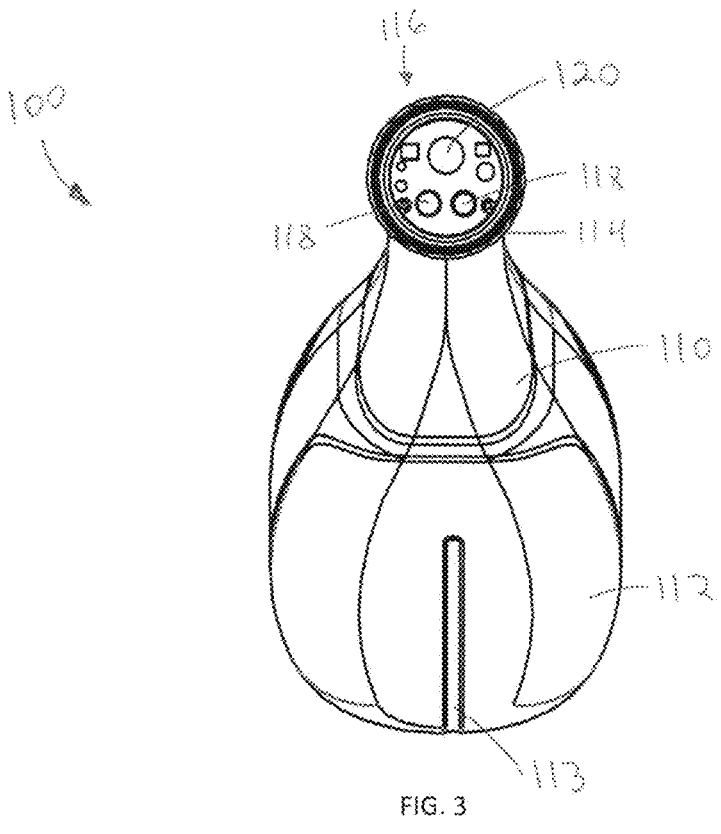
FIG. 3 is an end view of the handheld imaging device of FIG. 2.
Figure 4:
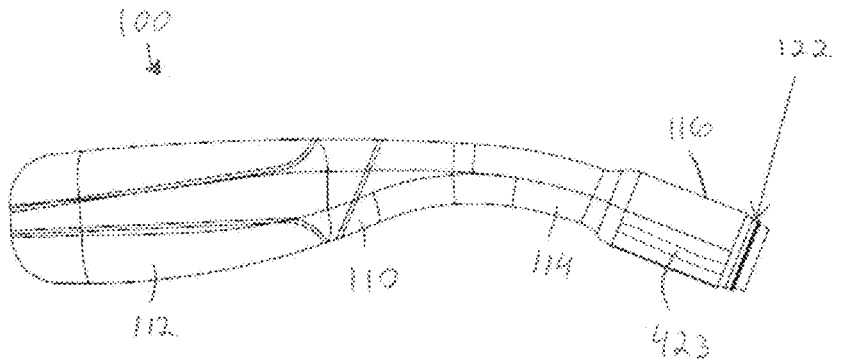
FIG. 4 is a side view of the handheld imaging device of FIG. 2.

In accordance with one aspect of the present disclosure, a handheld, fluorescence-based imaging device for visualization of tumor/cancer cells is provided. The fluorescence-based imaging device may include a body sized and shaped to be held in and manipulated by a single hand of a user. An exemplary embodiment of the handheld fluorescence-based imaging device is shown in FIGS. 2-4. As shown, in some example embodiments, the body may have a generally elongated shape and include a first end portion configured to be held in a user's hand and a second end portion configured to direct light onto a surgical margin on an outer surface of an excised tumor, on one or more sections of the excised tumor, or in a surgical cavity from which the tumor/tissue has been excised. The second end may be further configured to be positioned in a surgical cavity containing a surgical margin. The body of the device may comprise one or more materials that are suitable for sterilization such that the body of the device can be subject to sterilization, such as in an autoclave. An example of a suitable material is polypropylene. Those of ordinary skill in the art will be familiar with other suitable materials. Components within the body of the device that may not be capable of withstanding the conditions of an autoclave, such as electronics, may be secured or otherwise contained in a housing for protection, for example a metal or ceramic housing.

The device may be configured to be used with a surgical drape or shield. For example, the inventors have found that image quality improves when ambient and artificial light are reduced in the area of imaging. This may be achieved by reducing or eliminating the ambient and/or artificial light sources in use. Alternatively, a drape or shield may be used to block at least a portion of ambient and/or artificial light from the surgical site where imaging is occurring. In one exemplary embodiment, the shield may be configured to fit over the second end of the device and be moved on the device toward and away from the surgical cavity to vary the amount of ambient and/or artificial light that can enter the surgical cavity. The shield may be cone or umbrella shaped. Alternatively, the device itself may be enclosed in a drape, with a clear sheath portion covering the end of the device configured to illuminate the surgical site with excitation light. Other variations on a drape configured to reduce or remove ambient and/or artificial light may be used as will be understood by those of ordinary skill in the art. Additionally or alternatively, the handheld fluorescence-based imaging device may include a sensor configured to identify if lighting conditions are satisfactory for imaging. The device may also be used with a surgical drape to maintain sterility of the surgical field and/or to protect the tip of the device from body fluids. The surgical drape and ambient-light reducing drape may be combined into a single drape design. Alternatively, the surgical drape may envelope the device and the ambient-light reducing drape or shield may be positioned over the surgical drape.

The device may further include, contained within the body of the device, at least one excitation light source configured to excite autofluorescence emissions of tissue cells and fluorescence emissions of induced porphyrins in tissue cells of the surgical margin. The at least one excitation light source may be positioned on, around, and/or adjacent to one end of the device. Each light source may include, for example, one or more LEDs configured to emit light at the selected wavelength.

The excitation light source may provide a single wavelength of excitation light, chosen to excite tissue autofluorescence emissions and as well as fluorescence emissions of induced porphyrins in tumor/cancer cells contained in a surgical margin of the excised tumor/tissue and/or in a surgical margin of a surgical bed from which tumor/tissue cells have been excised. In one example, the excitation light may have wavelengths in the range of about 350 nm-about 600 nm, or 350 nm-about 450 nm and 550 nm-about 600 nm, or, for example 405 nm, or for example 572 nm.

Alternatively, the excitation light source may be configured to provide two or more wavelengths of excitation light. The wavelengths of the excitation light may be chosen for different purposes, as will be understood by those of skill in the art. For example, by varying the wavelength of the excitation light, it is possible to vary the depth to which the excitation light penetrates the surgical bed. As depth of penetration increases with a corresponding increase in wavelength, it is possible to use different wavelengths of light to excite tissue below the surface of the surgical bed/surgical margin. In one example, excitation light having wavelengths in the range of 350 nm-450 nm, for example 405 nm, and excitation light having wavelengths in the range of 550 nm to 600 nm, for example 572 nm, may penetrate the tissue forming the surgical bed/surgical margin to different depths, for example, about 500 $\mu$m-about 1 mm and about 2.5 mm, respectively. This will allow the user of the device, for example a surgeon or a pathologist, to visualize tumor/cancer cells at the surface of the surgical bed/surgical margin and the subsurface of the surgical bed/surgical margin. Additionally or alternatively, an excitation light having a wavelength in the near infrared/infrared range may be used, for example, excitation light having a wavelength of between about 750 nm and about 800 nm, for example 760 nm, 780 nm, or other wavelengths, may be used. In addition, to penetrating the tissue to a deeper level, use of this type of light source may be used in conjunction with a second type of imaging/contrast agent, such as infrared dye (e.g., IRDye 800, ICG). This will enable, for example, visualization of vascularization, vascular perfusion, and blood pooling within the surgical margins/surgical bed, and this information can be used by the surgeon in making a determination as to the likelihood that residual tumor/cancer cells remain in the surgical bed. In addition, the utility of visualizing vascular perfusion be to improve anastomosis during reconstruction.

The device may include additional light sources, such as a white light source for white light (WL) imaging of the surgical margin/surgical bed. In at least some instances, such as for example, during a BCS such as a lumpectomy, removal of the tumor will create a cavity which contains the surgical bed/surgical margin. WL imaging can be used to obtain an image or video of the interior of the cavity and/or the surgical margin and provide visualization of the cavity. The white light source may include one or more white light LEDs. Other sources of white light may be used, as appropriate. As will be understood by those of ordinary skill in the art, white light sources should be stable and reliable, and not produce excessive heat during prolonged use.

The body of the device may include controls to permit switching/toggling between white light imaging and fluorescence imaging. The controls may also enable use of various excitation light sources together or separately, in various combinations, and/or sequentially. The controls may cycle through a variety of different light source combinations, may sequentially control the light sources, may strobe the light sources or otherwise control timing and duration of light source use. The controls may be automatic, manual, or a combination thereof, as will be understood by those of ordinary skill in the art.

The body of the device may also contain one or more optical imaging filters configured to prevent passage of reflected excitation light and permit passage of emissions having wavelengths corresponding to autofluorescence emissions of tissue cells and fluorescence emissions of the induced porphyrins in tissue cells. In one example embodiment, the device includes one filter for white light (WL) imaging and infrared (IR) imaging, and another filter for fluorescence (FL) imaging. The device may be configured to switch between different imaging filters based on desired imaging mode and the excitation light emitted by the handheld device.

The handheld fluorescence-based imaging device also includes an imaging lens and an image sensor. The imaging lens or lens assembly may be configured to focus the filtered autofluorescence emissions and fluorescence emissions on the image sensor. A wide-angle imaging lens or a fish-eye imaging lens are examples of suitable lenses. A wide-angle lens may provide a view of 180 degrees. The lens may also provide optical magnification. A very high resolution is desirable for the imaging device, such that it is possible to make distinctions between very small groups of cells. This is desirable to achieve the goal of maximizing the amount of healthy tissue retained during surgery while maximizing the potential for removing substantially all residual cancer cells, precancer cells, satellite lesions. The image sensor is configured to detect the filtered autofluorescence emissions of tissue cells and fluorescence emissions of the induced porphyrins in tissue cells of the surgical margin. The image sensor may have 4K video capability as well as autofocus and optical and/or digital zoom capabilities. CCD or CMOS imaging sensors may be used. In one example, a CMOS sensor combined with a filter may be used, i.e., a hyperspectral image sensor, such as those sold by Ximea Company. Example filters include a visible light filter (https://www.ximea.com/en/products/hyperspectral-cameras-based-on-usb3-xispec/mq022hg-im-sm4x4-vis) and an IR filter (https://www.ximea.com/en/products/hyperspectral-cameras-based-on-usb3-xispec/mq022hg-im-sm5x5-nir). The handheld device also may contain a processor configured to receive the detected emissions and to output data regarding the detected filtered autofluorescence emissions of tissue cells and fluorescence emissions of the induced porphyrins in tissue cells of the surgical margin. The processor may have the ability to run simultaneous programs seamlessly (including but not limited to, wireless signal monitoring, battery monitoring and control, temperature monitoring, image acceptance/compression, and button press monitoring). The processor interfaces with internal storage, buttons, optics, and the wireless module. The processor also has the ability to read analog signals.

The device may also include a wireless module and be configured for completely wireless operation. It may utilize a high throughput wireless signal and have the ability to transmit high definition video with minimal latency. The device may be both Wi-Fi and Bluetooth enabled-Wi-Fi for data transmission, Bluetooth for quick connection. The device may utilize a 5 GHz wireless transmission band operation for isolation from other devices. Further, the device may be capable of running as a soft access point, which eliminates the need for a connection to the internet and keeps the device and module connected in isolation from other devices which is relevant to patient data security. The device may be configured for wireless charging and include inductive charging coils. Additionally or alternatively, the device may include a port configured to receive a charging connection.

Additional details regarding the construction, functionality, and operation of exemplary devices described here can be found in U.S. Provisional Applications 62/625,983 (filed Feb. 3, 2018) titled "Devices, Systems, and Methods for Tumor Visualization and Removal" and 62/625,967 (filed Feb. 3, 2018) titled "Devices, Systems, and Methods for Tumor Visualization and Removal," the entire contents of each of which are incorporated by reference herein.

Referring now to FIG. 1, a system 102 including a handheld imaging device 100 is shown. The handheld imaging device 100 is in communication with a hub 104, such as by wireless transmission (e.g., Wi-Fi, Bluetooth, or other wireless RF protocols). The hub 104 transmits imaging data received from the handheld imaging device 100 to a display monitor 106 for display using a protocol such as high-definition multimedia interface (HDMI). The hub 104 can also transmit the imaging data to a computer system 108, such as a terminal or a network for storage of the imaging data.

In accordance with one aspect of the present disclosure, an example embodiment of a handheld imaging device 100, in accordance with the present teachings, is shown in FIGS. 2-4. The handheld device 100 includes a body 110 having a first end portion 112 and a second end portion 114. The first end portion 112 is sized and shaped to be held in a single hand by a user of the device. The first end portion 112 may include controls 113 configured to actuate the device, toggle between and/or otherwise control different light sources, and switch between one or more optical imaging filters. Such controls can include buttons, switches, capacitive discharge sensors, or other devices to be manipulated by the user.

As illustrated in FIGS. 2-4, the second end portion 114 of the handheld device 100 may be tapered and/or elongated to facilitate insertion of a distal end or tip 116 of the second end portion through a surgical incision of 2-3 cm in size and into a surgical cavity from which a tumor or cancerous tissue has been removed. The second end portion 114 may be rigid and positioned at an angle relative to the first end portion 112 to facilitate better access under skin flaps, or may be configured to be flexible to facilitate imaging surgical cavities with complex geometries.

The distal end 116 includes one or more light sources 118, such as light-emitting diodes (LEDs) configured to emit light having a specific wavelength. For example, the one or more light sources 118 can be configured to emit wavelengths of 405 nm, 760 nm, 780 nm, or other wavelengths. The distal end 116 further includes an imaging device 120, such as a camera assembly configured to capture images of the surgical cavity illuminated by the one or more light sources 118. The distal end 116 further includes one or more spectral filters positioned to filter the light entering the imaging device 120, as discussed in greater detail below in connection with FIG. 5.

Figure 19:
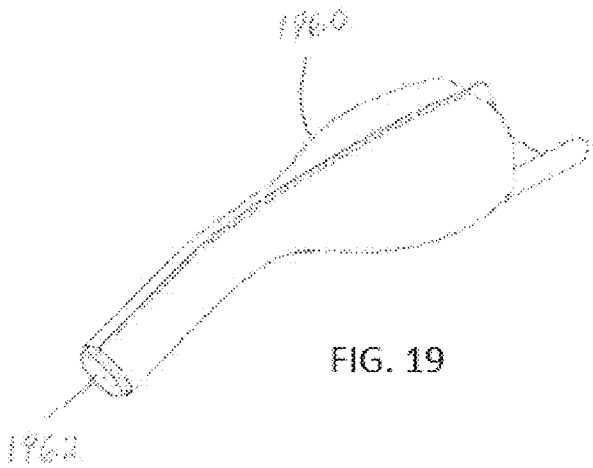
FIG. 19 is a perspective view of a sterile drape for a handheld imaging device according to the present disclosure.

The device 100 includes provisions to facilitate attachment of a drape to support sterility of the handheld device 100. For example, referring now to FIG. 19, a drape 1960 configured for use with the device 100 is shown. The drape 1960 may provide a sterile barrier between the non-sterile device contained in the drape and the sterile field of surgery, thereby allowing the non-sterile device, fully contained in the sterile drape, to be used in a sterile environment. The drape may cover the handheld device 100 and also provide a darkening shield that extends from the distal end (such as the distal end 116) and covers the area adjacent the surgical cavity to protect the surgical cavity area from light infiltration from sources of light other than the handheld device 100. The drape can also include or be coupled with a hard optical window, such as lens cap 1962 (or, in other embodiments, lens cap 524 discussed further below in connection with FIG. 5), that covers the distal end of the handheld device 100 to ensure accurate transmission of light emitted from the light sources 118 and corresponding transmission of light back to the imaging device 120. The body of the drape 1960 can comprise a polymer material, such as polyethylene, polyurethane, or other polymer materials. Optionally, the lens cap 1962 can comprise a different material, such as polymethyl methacrylate (PMMA) or other rigid, optically transparent polymers, glass, silicone, quartz, or other materials.

Figure 20:
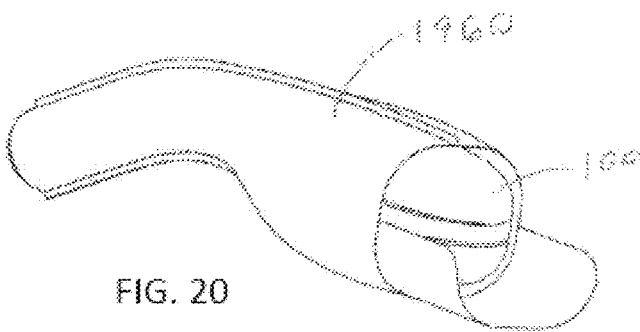
FIG. 20 is a perspective view of the sterile drape of FIG. 19 with a handheld imaging device inserted in the sterile drape.
Figure 21A:
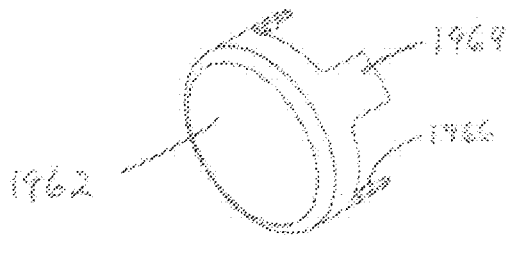
FIG. 21A is a perspective view of a lens cap portion of the surgical drape of FIG. 19.
Figure 21A:
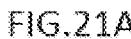
Figure 21B:
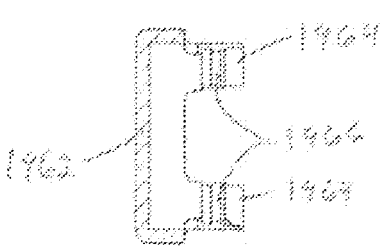
FIG. 21B is a cross-sectional view of the lens cap portion of FIG. 21A.

Referring now to FIG. 20, the device 100 may be inserted within the drape 1960 to protect the device 100 from exposure to the surgical environment and to ensure the non-sterile device does not contaminate the sterile surgical field. The drape 1960 may be coupled to the device 100 with a retaining device. As shown in FIG. 4, the distal end 116 of the handheld device 100 includes a circumferential groove 122 configured to interact with one or more features of the drape 1960 to retain the drape 1960 on the handheld device. For example, referring now to FIGS. 21A and 21B, the lens cap 1962 can optionally include features that the engage the groove 122 (FIG. 4.). In the embodiment of FIGS. 21A and 21B, the lens cap 1962 includes a plurality of legs 1964, each of which features an engagement tang 1966 that is configured to engage the groove 122 (FIG. 4) when the lens cap 1962 is placed over the distal end 116 of the device 100. Additionally or alternatively, the drape may include a device such as a retaining ring or band to hold the drape on the handheld device 100. The retaining ring can be or include a resilient band, a snap ring, or similar component.

In some embodiments, the handheld device 100 can include a built-in display screen in place of, or in addition to, the link to the hub 104 (FIG. 1). For example, the built-in screen could eliminate the need for an external display device such as display 106 and/or computer system 108, or could provide additional information to the user, such as a mode in which the handheld device 100 is operating. Further, the display information could be additionally or alternatively provided to a head-mounted display for augmented reality (AR) or virtual reality (VR) surgery, including remote and/or robotic surgeries, or projected onto a holographic display.

Referring again to FIG. 4, in some exemplary embodiments, the handheld device 100 can include a channel 423 formed in a lateral wall of the distal end 116. The channel 423 can be used to facilitate insertion of additional tools, such as optical fibers for an auxiliary light source or auxiliary imaging sensor, a cauterizing tool, biopsy forceps, a tagging tool (for marking tissue with a clip, optical tag, dye or paint, etc.), or other tools, while the handheld device 100 is in position within a surgical site. Alternatively or additionally, some embodiments could include a channel formed within the distal tip 116 of the device 100, i.e., an internal channel within the device for introduction of any of the above-mentioned tools into the surgical site while the handheld device 100 is in use.

The handheld device 100 can also include provisions to facilitate stand-mounting of the device 100 while in use. For example, while the handheld device 100 may be designed and constructed primarily for handheld use, under some circumstances it may be desired to place the handheld device 100 on a stand or fixed mount, e.g., during use in which different images of the same tissue are being taken, to ensure the context and position of the image is consistent across multiple images. The handheld device can be coupled to a stand, such as a gooseneck-type flexible stand with a weighted or clamp-type mount to hold the assembly in place on a desk or operating table. In other embodiments, the stand mount could be cart-based and could be moved outside the surgical sterile field while holding the device. The stand mount can enable the device to be used without the user holding it in the user's hand. The stand could be configured to hold additional, auxiliary light sources, imaging devices, supporting tools such as biopsy forceps, tagging tools, or other devices.

Referring now to FIG. 5, a perspective view of a distal end 516 of a handheld device according to an embodiment of the present disclosure is shown. The distal end 516 can be fitted with a sterile lens cap 524. The lens cap 524 can be coupled with a drape as discussed above, and the drape can be configured to cover the body of the handheld device and to provide a light shield extending from the distal end of the handheld device to prevent ambient light from entering the area to be imaged by the handheld device. Similar to the embodiment of the lens cap 1962 of FIGS. 21A and 21B discussed above, the lens cap 524 can include one or more features configured to engage features of the distal end of the handheld device, such as by engaging the groove 122 shown in FIG. 4.

As discussed in greater detail below, the handheld device includes various electrical subsystems including one or more imaging devices, such as camera sensors, one or more fluorescent light LEDs, one of more infrared LEDs, one or more white light LEDs, and various sensors such as temperature sensors, ambient light sensors, and range finding sensors. Other components can include one or more of LED drivers that generate drive voltages to drive the LEDs as required to achieve the setpoint drive current, one or more accelerometers and gyroscopes to allow a video stream to be tagged with the position of the handheld device, e.g., to provide spatial orientation of features within the surgical cavity, flash memory to provide local storage of videos and still images, a USB hub to provide an interface for factory load of software, test, and calibration of the handheld device, an inductive battery charging system, motor drive electronics to provide automatic switching of optical filters as discussed below, a Wi-Fi radio subsystem, a user interface providing information regarding to mode the device to the user, a rechargeable battery (such as a Li-Ion battery), an audio device such as a speaker for providing audible feedback of the system state to the user, and other components. Such components can be operatively coupled with one or more controllers, such as computer processors, housed within the handheld device.

For example, in an embodiment, the handheld device includes one or both of an application processer and a microcontroller unit. The application processor can perform functions including, but not limited to, sending the camera interface and video stream (e.g., still images and motion video) to the wireless transmission function to transmit the data to a display or computer terminal, interfacing with the accelerometer, gyroscope, and on-board flash memory, interfacing with the microcontroller unit, driving the speaker for audible feedback to the user, and managing the wireless communications subsystem.

The microcontroller unit can provide functions such as control the LED drive electronics including the temperature compensation loops, communication with the temperature sensor, the ambient light sensor, and the range finder, and interfacing with the application processor for conveying and receiving system usage and context state. The microcontroller unit can also monitor the system for exception conditions, control indicator LEDs, control pushbuttons or other user interface devices, control the motor drive for switching between optical filters, monitor the wireless battery charging and charge state and control power management, as well as other functions.

Referring now to FIG. 6, the handheld device distal end portion 516 shown in FIG. 5 is shown in end view. The handheld device 500 comprises an imaging device 520 that may be or include a camera, such as a charge-coupled device (CCD), a complementary metal-oxide-semiconductor (CMOS) device, or other image capture technology, such as imaging devices including a hyperspectral image sensor module. As shown in FIG. 5, the imaging device 520 is in an offset position on the end of the handheld device 500. While the embodiment of FIGS. 5 and 6 includes a single imaging device 520, other exemplary embodiments of the present disclosure could include two or more separate imaging devices to support additional imaging modes.

The handheld device 500 further includes a diffuser 522 that diffuses light produced by light sources, e.g., LEDs similar to the LEDs 118 discussed in connection with the embodiment of FIGS. 2-4. The diffuser 522 can be configured to ensure that the light leaving the handheld device 500 is sufficiently diffuse to evenly illuminate the target area (e.g., surgical cavity) and provide even excitation of the tissue. The diffuser 522 can be made from a polymer material that scatters light emitted by the LEDs into a more homogenous output. The diffuser 522 can comprise material such as, e.g., acrylic, polycarbonate, mylar, plastic films, or other materials. The diffuser 522 may be shaped such that it does not block other components at the distal end of the device 100, such as the temperature sensor, range finder, ambient light sensor, or other components described in connection with FIG. 8 below.

Figure 9:
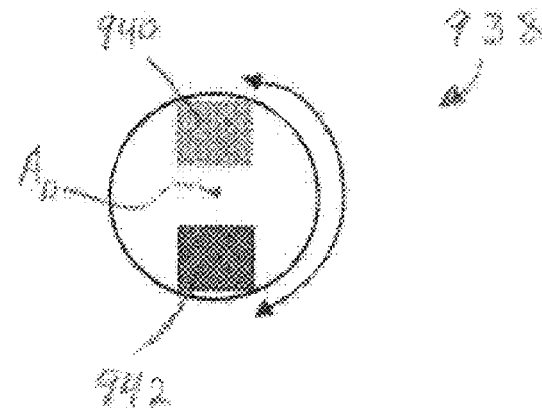
FIG. 9 is a schematic view of a rotatable light filter portion of a handheld imaging device according to an embodiment of the present disclosure.

The handheld device can include one or more printed circuit board (PCB) components to facilitate manufacture and assembly of the handheld device. For example, referring now to FIG. 7, the distal end 516 of the handheld device 500 is shown in exploded view, showing multiple PCB components for mounting and interconnecting various electronic components. The handheld device 500 includes an LED PCB 726 that can include one or more light emitting diodes (LEDs) 718 and associated electrical components. The LED PCB 726 can be operatively coupled with other electronic systems in the handheld device through wiring (such as a bus), and can be connected to control systems of the handheld device 500 such as controls 113 (FIG. 2) a power source such as a battery, etc. The distal end 516 can include an electric motor drive system 727 for rotating the filter wheel 938 discussed below in connection with FIG. 9.

A distal PCB 728 can be positioned adjacent the imaging device 520 and can include components supporting the imaging device 520, such as components that interface the imaging device 520 with the controls 113 (FIG. 2) and a power supply, e.g., battery, of the handheld device 500. In some embodiments, the light sources 118 (FIG. 2) of the handheld device can be included on the distal PCB 728.

Figure 8:
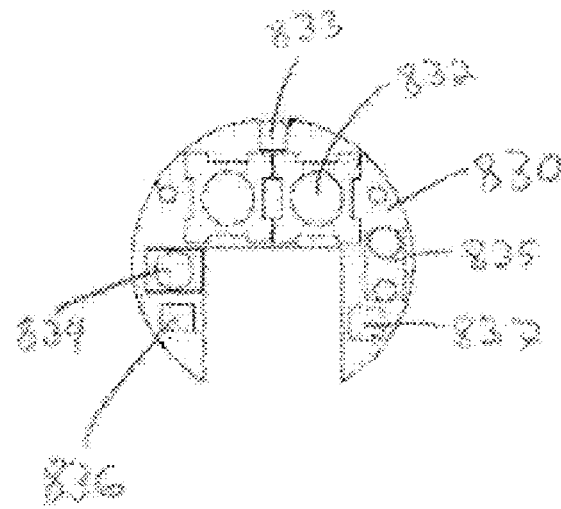
FIG. 8 is a plan view of a distal end PCB of a handheld imaging device according to an embodiment of the present disclosure.

For example, with reference now to FIG. 8, an exemplary layout for a distal end PCB 830 is shown. In the embodiment of FIG. 8, the PCB 830 includes first and second LED devices 832 and 834. As a non-limiting example, the first and second LED devices 832 can comprise an LED configured to emit light having a 405 nm wavelength, while the second LED device 834 can comprise an LED configured to emit light with a 760 nm wavelength, a 780 nm wavelength, or other wavelengths. The PCB 830 can further include a white light LED 836 configured to provide visual illumination to the area to be imaged.

As will be understood by those of skill in the art, the arrangement of the components in the distal end of the imaging device may take on many configurations. Such configurations may be driven by size of the device, the footprint of the device, and the number of components used. However, when arranging the components, functional factors should also be considered. For example, issues such as light leakage from light sources of the device and/or an ambient light entering the housing may interfere with proper or optimal operation of the device, and may for example cause a less desirable output, such as image artifacts. The arrangements illustrated in FIGS. 6-8 and elsewhere herein represent example arrangements in which camera sensors are isolated so as to prevent light leakage from light sources and ambient light.

The distal PCB can include other components operatively coupled with a control system of the handheld device and configured to provide other information to the control system to support effective operation of the handheld device. For example, the distal PCB 830 can include a temperature sensor 833 used to provide feedback to an LED setpoint temperature compensation loop to ensure the system is operating within a safe temperature range and to minimize the effect of temperature change on LED radiant flux. LED radiant flux efficiency on target optical power as a function of LED drive current is temperature dependent, so the temperature compensation loop adjusts the nominal LED drive setpoint as a function of temperature to facilitate maintaining constant radiant flux over temperature. The temperature control loop can be realized in software running on the microcontroller unit, fully in hardware, or a combination thereof.

A range finder 835 can measure the distance between the camera sensor and the target being imaged and can be used to provide feedback to the user to guide the user on imaging at the correct distance. A change in measured target distance can optionally be used to initiate a camera sensor refocus action. An ambient light sensor 837 can provide feedback to user regarding the level of ambient light, as the fluorescence imaging is only effective in an adequately dark environment. The measured ambient light level could also be useful during white light imaging mode to enable the white light LED or control its intensity. The distal PCB 830 can be operatively coupled with other portions of the handheld device, such as the controls 113 (FIG. 2), a power supply such as a battery, one or more processors, such as the microcontroller unit and the application processor, or other components.

The LED devices 832, 834, and 836 can be controlled by a closed-loop system using information from the temperature sensor as input to a control loop which adjusts the LED drive current setpoint. In some embodiments, low and high range LED intensity modes may be supported for different applications. Examples include imaging at close range within a surgical cavity and lumpectomy imaging in the pathology suite at far range.

As noted above, the handheld device can include one or more optical filters configured to permit passage of a specific light wavelength or wavelength band while blocking other wavelengths. By positioning such a filter between the imaging device 520 (FIG. 6) and the area to be imaged, a particular wavelength or band of wavelengths is isolated in the image and permits visualization of the areas emitting light in that wavelength or wavelength band. For example, the handheld device can include one or more of a notch filter configured to pass a specified wavelength, a filter configured to transmit green (approximately 500-550 nm light) and red (approximately 600-660 nm) wavelengths, or other types of optical spectral filters. One example of an optical filter configured to transmit green and red wavelengths is available from CHROMA® Technology Corp., 10 Imtec Lane, Bellows Falls VT, 05101 USA, part no. 59022m. The one or more filters may be configured such that the user can switch between the one or more filters when using different light sources, different compounds or dyes, etc. Such switching of filters can be carried out automatically based on other user-defined settings of the handheld device, such as a mode chosen by the user.

The device may be modified by using optical or variably oriented polarization filters (e.g., linear or circular combined with the use of optical wave plates) attached in a reasonable manner to the excitation/illumination light sources and the imaging sensor. In this way, the device may be used to image the tissue surface with polarized light illumination and non-polarized light detection or vice versa, or polarized light illumination and polarized light detection, with either white light reflectance and/or fluorescence imaging. This may permit imaging of tissues with minimized specular reflections (e.g., glare from white light imaging), as well as enable imaging of fluorescence polarization and/or anisotropy-dependent changes in connective tissues (e.g., collagens and elastin) within the tissues. The ability to use polarization optics in the device enables either polarization of reflected light or fluorescence light from a target. This may potentially provide improved image contrast where tumor vs normal tissues reflect 405 nm excitation light differently or emit different polarization information from the 500-550 nm and 600-660 nm emitted fluorescence light.

The handheld device can include components configured to enable filters to be switched quickly in a manual or automatic fashion. For example, referring now to FIG. 9, a filter wheel 938 in accordance with an embodiment of the present disclosure is shown. The filter wheel can be positioned on the handheld device between the imaging device (e.g., imaging device 520) and the area to be imaged. For example, in the embodiment of FIGS. 5 and 6, a filter wheel can be distal of the imaging device 520 in the distal end 516 of the handheld device.

The filter wheel 938 includes a first optical filter 940 configured to support white light and infrared (WL/IR) imaging, and a second optical filter 942 configured to support fluorescence (FL) imaging. The first filter 940 and second filter 942 are positioned opposite one another across a rotational axis AR of the filter wheel 938 about which the filter wheel 938 is rotatable. As discussed above, the imaging device 520 (FIG. 6) can be in an offset position such that each of the first filter 940 and second filter 942 can alternatingly be positioned in front of the imaging device 520 as desired by the user. The filter wheel 938 can be rotated by an internal electromechanical system controllable by the user, such as a motor and pinion gear meshing with a gear on the filter wheel 938 or another mechanism configured to rotate the filter wheel 938. As discussed in greater detail below in connection with FIGS. 10-15, the user can choose one of the first filter 940 and second filter 942 based on the compound or dye used and/or the wavelength of the excitation light applied to the surgical cavity. Additionally or alternatively, rotation of the filter wheel 938 can be done manually, such as by providing on the filter wheel 938 a circumferential surface that can be gripped by a user. While the filter wheel 938 shown in FIG. 9 includes two filters, other embodiments of filter wheels could include three filters, four filters, or any desired number of desired filters that can be fit on the filter wheel 938.

In an exemplary embodiment, the first filter 940 comprises a notch filter configured to block light having a wavelength of from 675 nm to 825 nm, while allowing passage of wavelengths less than 675 nm and greater than 825 nm. In a different embodiment, the first filter 940 can comprise a notch filter configured to block light having a wavelength of from 690 nm to 840 nm, while allowing passage of wavelengths less than 690 nm and greater than 825 nm. The second filter 942 can comprise an optical filter that transmits green and red light, e.g., the filter having the characteristics discussed in connection with FIGS. 12-15 below.

Figure 30:
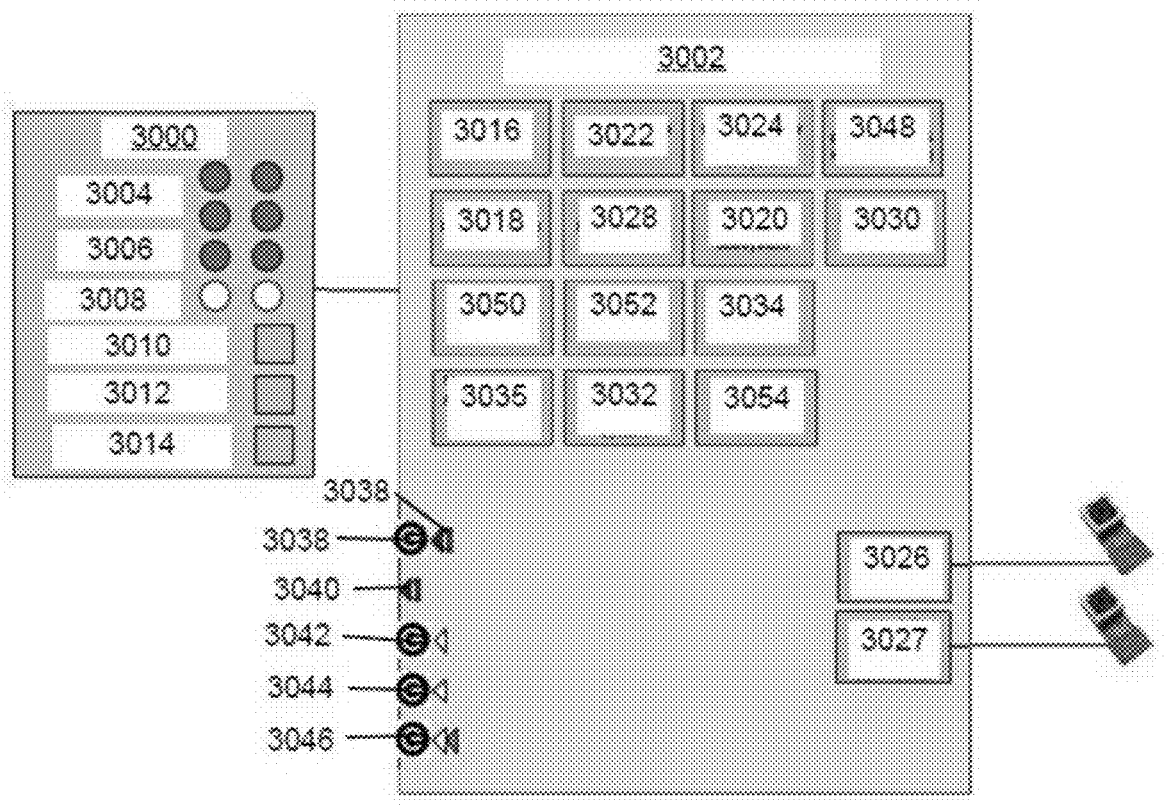
FIG. 30 is a block diagram showing hardware components of a handheld imaging device according to an exemplary embodiment of the present disclosure.

Referring now to FIG. 30, a block diagram showing the various components of a handheld imaging device according to an exemplary embodiment of the present disclosure is shown. In the diagram of FIG. 30, the components are grouped in an optical PCB 3000 and an electronics system 3002. In the embodiment of FIG. 30, the optical PCB includes 4 fluorescent wavelength LEDs 3004, 2 infrared LEDs 3006, and two white light LEDs 3008. The optical PCB further includes an ambient light sensor 3010, a laser range finder 3012, and a temperature sensor 3014.

The optical PCB 3000 is operably coupled with the electronics system 3002. The electronics system 3002 can include, for example and without limitation, electronic control components such as an application processor module 3016, a real time microcontroller unit (MCU) 3018, and a power management subsystem 3020. The electronics system 3002 can further include components and systems that interface with other electronic components of the handheld imaging device. For example, the electronics system 3002 can include a CMOS camera interface 3022 and motor drive electronics 3024 for the optical filter system. The electronics system can also include connectors 3026 and 3027 for the fluorescent and white light cameras, respectively, to facilitate switching between the fluorescent and white light imaging modes discussed herein.

Other supporting electronic systems and components of the electronics system 3002 can include memory, such as a flash memory device 3028, a rechargeable battery such as a lithium-ion battery 3030, and an inductive battery charging system 3032. Some components of the electronics system 3002 can include communications components, such as Wi-Fi and/or Bluetooth radio subsystem 3034, and spatial orientation components such as one or more of magnetometers, accelerometers, and gyroscopes 3035.

The electronics system 3002 can include various user controls, such as a power switch 3036, system status LEDs 3038, charging status LEDs 3040, a picture capture switch 3042, video capture switch 3044, and imaging mode switch 3046. The various user controls can interface with the other components of the electronics system through a user interface module 3048 that provides signals to and from the user controls.

Other components in the electronic system 3002 can include drivers 3050 for the fluorescent, infrared, and white light LEDs, a USB hub 3052 for uplink or downlink data signals and/or power supply from an external computer system to which the electronic system 3002 can be connected through the USB hub 3052, such as a workstation or other computer. The electronics system 3002 can also include one or more devices that provide feedback to a user, such as, without limitation, a speaker 3054. Other feedback devices could include various auditory and visual indicators, haptic feedback devices, displays, and other devices.

Figure 31:
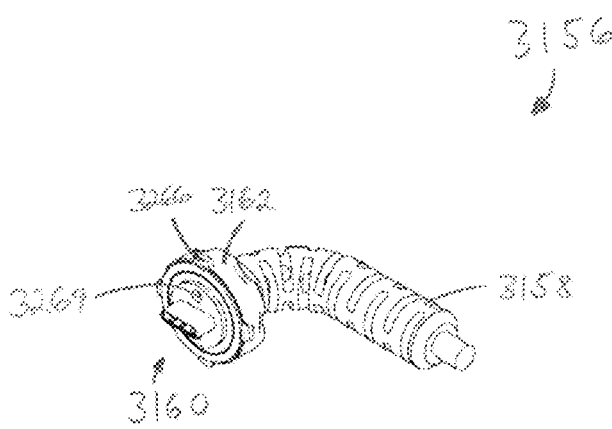
FIG. 31 is a perspective view of a USB connector according to an exemplary embodiment of the present disclosure.

The electronic system 3002 (FIG. 30) can be operatively coupled to a computer by the USB hub 3052 (FIG. 30) through a removable USB connection cable 3156 as shown in FIG. 31. The cable 3156 can include various features configured to ensure that the cable does not interfere with the surgical field and to ensure the cable is not inadvertently removed from the handheld device during use. While the description herein may refer to universal serial bus (USB) type connections, it should be understood that the present disclosure is not limited to any specific connection protocol, and connection protocols other than the various types of USB interfaces are within the scope of the disclosure.

The cable 3156 can include a strain relief feature 3158 molded to facilitate keeping the cable from interfering with the surgical field. For example, in the embodiment of FIG. 31, the cable 3156 is configured to be inserted into a connection port on the back of a handheld device according to the present disclosure. The strain relief 3158 is molded to create a general 90-degree curvature in the cable 3156 when in an unstressed state. The curvature of the cable 3156 facilitates routing of the cable 3156 away from the surgical field. The curvature of the cable may be less than or greater than 90 degrees. As an exemplary range, the curvature of the cable can be, without limitation, from 70 degrees to 110 degrees. Curvatures of less than 70 degrees or greater than 110 degrees are within the scope of the disclosure. The particular shape of the cable imparted by the strain relief feature 3158 can depend on the location of the connection port on the handheld device. For example, for a handheld device with a connection port on the side, the strain relief feature could be straight to route the cable away from the surgical field.

The cable 3156 can also include a connection interface 3160 configured to electrically and mechanically couple the cable 3156 to the handheld device. The connection interface 3160 can include a locking ring 3162 that provides a positive mechanical engagement between the cable 3156 and the handheld device to prevent the cable 3156 from being inadvertently pulled from the handheld device during use.

Figure 32:
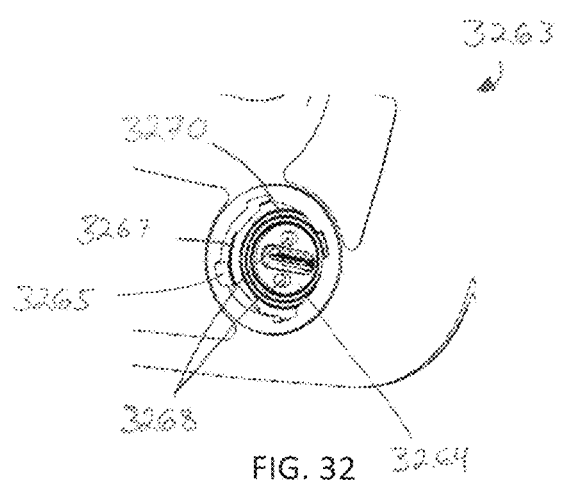
FIG. 32 is a perspective view of a housing of a handheld device according to an exemplary embodiment of the present disclosure with a USB port configured to receive the USB connector of FIG. 31.

For example, referring now to FIG. 32, a portion of a housing 3263 is shown, including a connection port 3264 configured to receive the connection interface 3160 of the cable 3156. The connection port 3160 includes a surrounding portion including slots 3265 configured to receive corresponding tabs 3266 of the locking ring 3162. After the locking ring 3162 is inserted such that the tabs 3266 of the locking ring 3162 are received in the slots 3265, the locking ring 3162 is rotated such that the tabs 3266 rotate into circumferentially extending portions 3267 of the slots 3265, and the locking ring 3162 retains the connection interface 3160 within the connection port 3264.

The locking ring 3162 and the surrounding portion can comprise materials having sufficient mechanical strength to withstand forces that may be applied to the connection interface 3160 in use. For example, one or both of the locking ring 3162 and the surrounding portion of the connection port 3264 can comprise a metal such as an aluminum alloy, a high strength polymer, composite material, or other material.

Because the strain relief feature 3158 routes the cable away from the handheld device, application of force to the cable 3156 and/or strain relief feature 3158 can create a relatively large torque at the connection interface 3160 due to the strain relief feature 3158 acting as a moment arm. The connection interface 3160 of the cable 3156 and a corresponding connection port on the housing of the handheld device can include features configured to withstand such torque and other forces without applying these forces to the more sensitive electrical contact components of the connection interface 3160 and corresponding connection port.

For example, the connection port 3264 can include pins 3268 extending from a face of the port 3264. The connection interface 3160 of the cable 3156 includes recesses 3269 (only one of which is shown in FIG. 32) into which the pins 3268 are received. The pins 3268 and recesses 3269 form a mechanical interface between the connection port 3264 and connection interface 3160 that has mechanical strength sufficient to withstand typical forces to which the cable 3156 and connection port 3264 are subjected during use and prevents undue stress from being placed on the electrical interface components of the connection port 3264 and connection interface 3160.

Additionally, in some exemplary embodiments, one or both of the connection port 3264 and the connection interface 3160 can include a seal to prevent intrusion of various contaminants such as biological or therapeutic liquids or substances into the electrical contacts of the connection port 3264 and connection interface 3160. For example, in the embodiment of FIG. 32, the connection port 3264 includes a gasket 3270 that forms a seal against the connection interface 3160 when the connection interface 3264 is secured in the connection port 3264 with the locking ring 3162. Additionally, in some embodiments, the gasket or other seal can be configured to provide a preload force between the connection port 3264 and connection interface 3160 that serve to keep the locking ring 3162 secure in a coupled state of the connection interface 3160 in the connection port 3264. When in the coupled state, the cable 3156 can provide a data and/or power transmission conduit for the handheld device to be attached to a computer, as discussed above. Further, the cable 3156 can be provided with a sterile sheath configured to attach to the sterile drape 1960 (FIG. 19) to maintain a sterile barrier between the handheld device 100 and the surgical field when the cable 3156 is coupled to the connection port 3264.

Figures 10, 11:
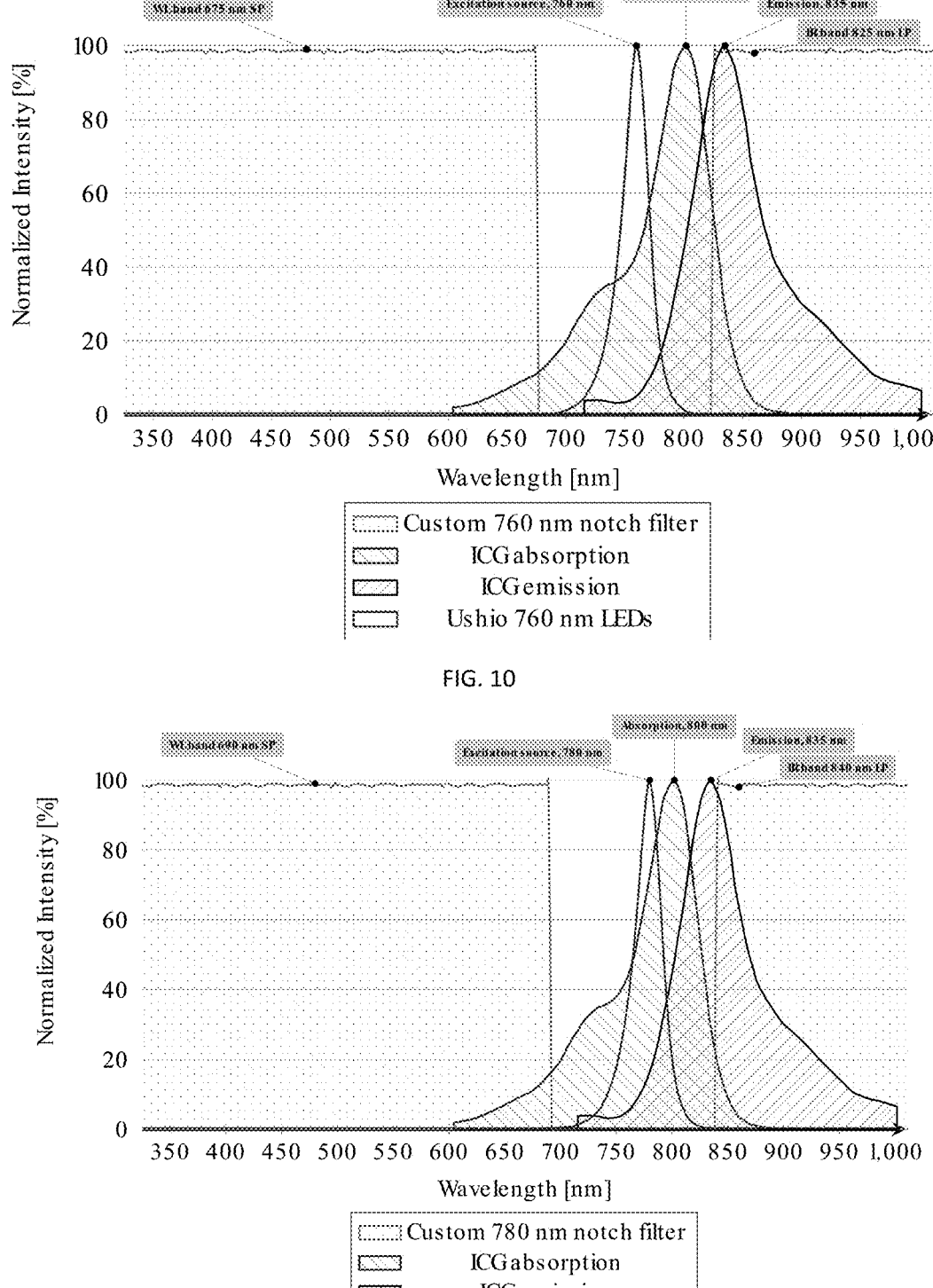
FIGS. 10-15 are charts showing exemplary bands of various filters configured to detect emissions excited by an excitation light and incorporated into embodiments of the handheld imaging device according to the present disclosure.

FIGS. 10-15 provide examples of potential usage scenarios of the handheld device according to various embodiments of the disclosure. Referring now to FIG. 10, in this usage scenario, the tissue is illuminated with a light source (such as one or more LEDs 118 (FIG. 2) of the handheld device 100) providing an excitation light wavelength of 760 nm. The tissue is treated with an IR dye such as ICG. A filter positioned to filter light entering an imaging device, such as imaging device 520 (FIG. 6) comprises a 760 nm notch filter that filters the excitation light from being captured by the image sensor. The filter has a notch between 675 nm and 825 nm. As seen in the chart of FIG. 10, the light emitted from the ICG-treated tissue has an emission wavelength of 835 nm, and thus passes through the notch filter and is captured by the image sensor, thereby generating an image with revealing the ICG-treated tissue.

Referring now to FIG. 11, tissue is illuminated with a light source having a wavelength of 780 nm. A notch filter having a short pass wavelength of 690 nm and a long pass wavelength of 840 nm is used to filter light returning to the imaging device. The tissue is treated with an IR dye such as ICG, and when excited by the 780 nm light source, emits a light with a peak intensity wavelength of 835 nm and passes through the notch filter to be captured by the imaging device, again revealing the ICG-treated tissue in the resulting image.

Figure 12:
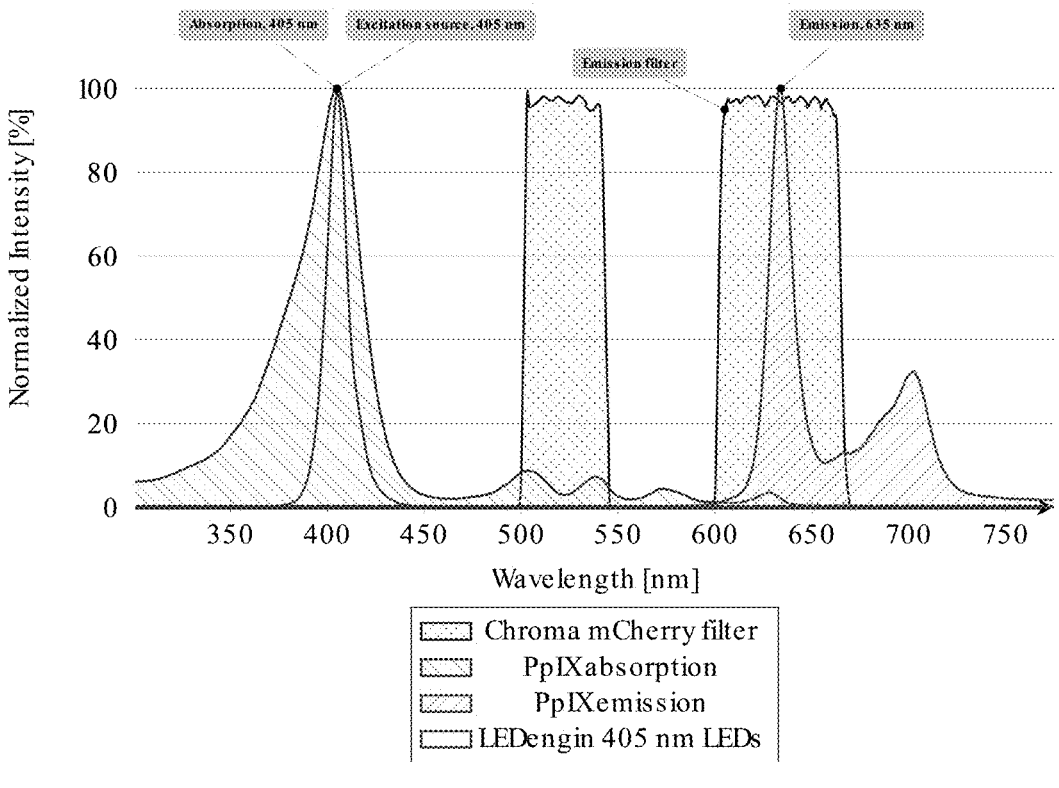

FIGS. 12-15 are example use scenarios where the handheld device is used for fluorescence imaging to improve tumor-to-normal contrast. Referring now to FIG. 12, the subject may be given a diagnostic dose of aminolevulinic acid (ALA) to induce PpIX formation in tumor tissue. The tissue is illuminated with a light source having a wavelength of 405 nm. A CHROMA® filter that transmits green and red wavelengths is used to filter light captured by the imaging device. As shown in FIG. 12, the PpIX emits light with a wavelength of 635 nm, within the red transmission band of the filter, and thus can be captured by the imaging device, revealing in the resulting image the tissue in which PpIX formation was induced.

Figure 13:
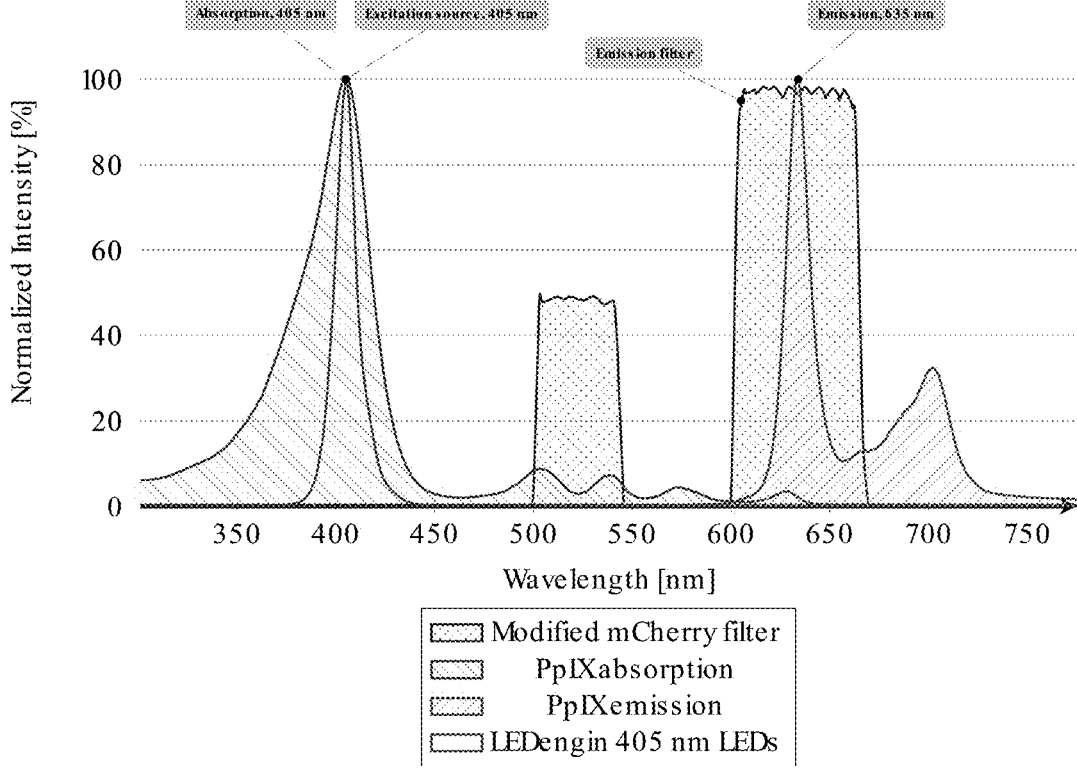
Figure 14:
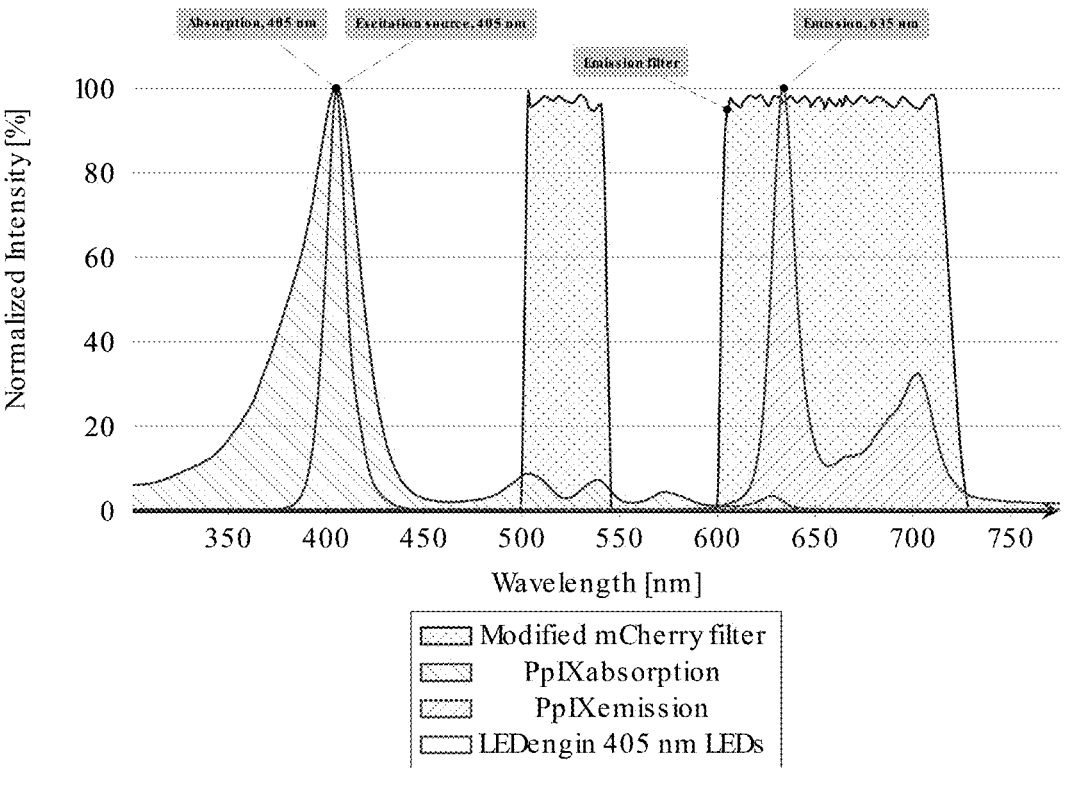
Figure 15:
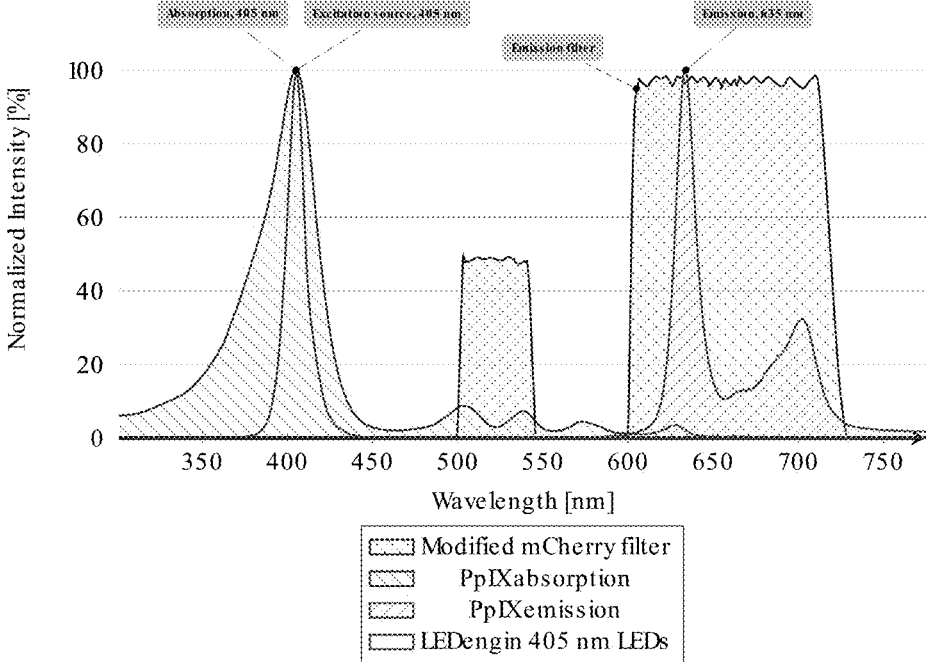

FIGS. 13-15 present examples similar to the example of FIG. 12, with various modifications made to the filter used in FIG. 12 to improve tumor-to-normal contrast. In FIG. 13, the filter is modified to reduce the green band transmission by approximately 50%. In other embodiments, the reduction of green band transmission may be less than or greater than 50%, such as any amount in the range of from about 10% to about 90%, less than 10%, or greater than 90%. In FIG. 14, the filter is modified to widen the red transmission band to 600-725 nm (from approximately 600-675 nm shown in FIGS. 12 and 13). In FIG. 15, the filter is modified both to reduce the green band transmission by 50% and to widen the red band transmission to 725 nm.

According to embodiments of the disclosure, changing from the white light and infrared imaging modes discussed in connection with FIGS. 10 and 11 to the fluorescence imaging modes discussed in connection with FIGS. 12-15 can be accomplished by rotating the filter wheel 938 (FIG. 9) such that the desired filter (e.g., the notch filter or the filter that transmits green and red wavelengths) is positioned in front of the imaging device to filter the light wavelengths returning to the handheld device. Controls on the handheld device, such as controls 113 (FIG. 2) can include switches, buttons, etc. to switch light sources from the 760 nm or 780 nm LEDs to the 405 nm LEDs or to the white light LEDs. In some embodiments of the disclosure, the filter wheel can be configured to automatically rotate from one filter to another based on a chosen mode of the handheld device, e.g., input by a user at the controls 113.

The handheld device can be further configured to provide imaging modes in addition to those described above. For example, the handheld device can include a mode in which the image sensor, the light source, and the filter are configured to provide 3D imaging for topographic mapping of an imaging surface. Additional details regarding the use of 3D imaging can be found in U.S. Provisional Application No. 62/793,837 titled "Systems, Methods, and Devices for Three-Dimensional Imaging, Measurement, and Display of Wounds and Tissue Specimens," (filed Jan. 17, 2019), the entire contents of which are incorporated by reference herein.

As an example of another imaging mode, the handheld device can be configured to provide fluorescence lifetime imaging of tissue. Fluorophores such as PpIX have a fluorescence emission decay profile that defines how quickly the visible fluorescence light will die out once the excitation source is removed. Thus, by capturing images shortly after excitation sources are removed or turned off, different fluorophores can be imaged in isolation by tailoring an image capture time for each unique fluorophore after the excitation source that excited the specific fluorophore is removed. For example, if PpIX and another fluorophore have decay times of 9 ns and 5 ns respectively, PpIX can be imaged in isolation by capturing an image between 5 and 9 ns after the excitation source is removed. In this manner, fluorescence lifetime imaging can enable detection of multiple unique fluorophores by their respective fluorescence lifetime signatures based on the differences in the exponential decay rate of the fluorescence from the fluorophore. Such time-resolved fluorescence imaging methods could be achieved by pulsing various excitation wavelength LEDS and gating imaging sensors to detect fluorophore lifetimes of interest. Fluorescence lifetime imaging of tissue could be used to identify and differentiate between different tissue components, including healthy and diseased tissues but also other biological components such as microorganisms and intrinsically-fluorescent chemical agents or drugs.

Other possible imaging modes could include various combinations of white light imaging, infrared imaging, and fluorescence imaging. For example, in one possible imaging mode, both white light and IR light sources are used to illuminate the tissue. An infrared dye, such as ICG, may be excited by the IR light source and the resulting IR imagery can be overlaid on the white light image to show the IR imagery in anatomical context.

Figure 16:
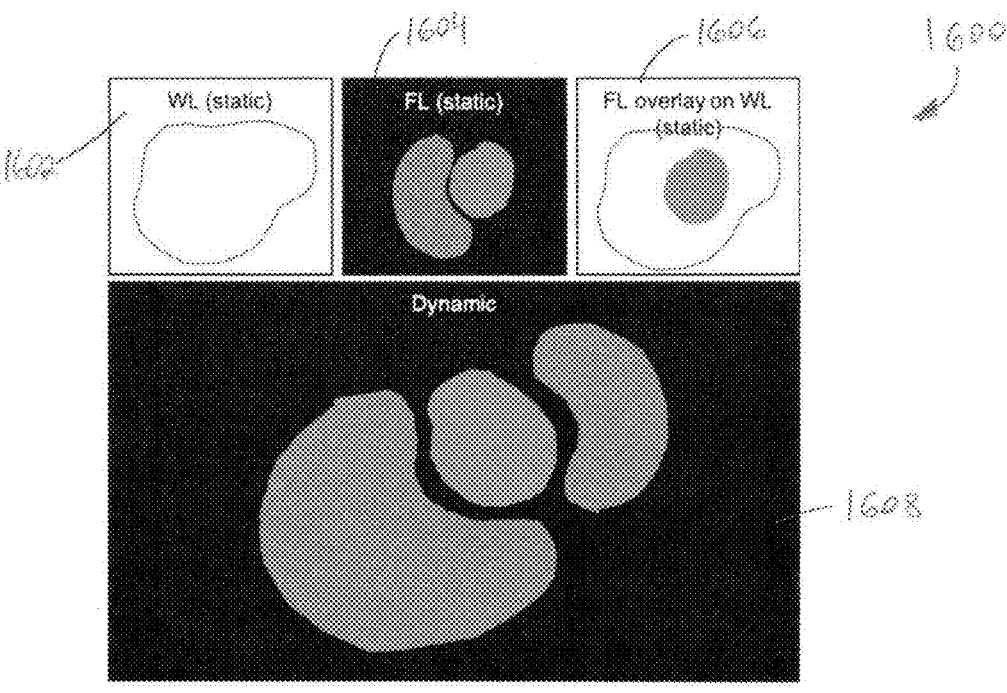
FIGS. 16-18 are exemplary display layouts associated with various imaging modes of the handheld imaging device of the present disclosure.

In another imaging mode, white light illumination is followed by 405 nm light illumination. The imaging filter for WL/IR is used during white light illumination, and the FL filter is used during 405 nm illumination. Sequential images of white light and fluorescence are captured and can be overlaid to provide anatomical context (white light image) for the tumor location (FL image). For example, as shown in FIG. 16, a display 1600 may be partitioned into several panels. Panel 1602 displays a static white light image, while panel 1604 displays a static fluorescence image. Panel 1606 displays an image with the fluorescence image overlaid on the white light image. Panel 1608 displays a dynamic display that can be switched between white light and fluorescence imagery as desired. With the dynamic panel 1608 in fluorescence mode, then the user would scan the cavity/sample to find the fluorescent tumor tissue, and possibly tag the tissue with a vascular clip or similar. The fluorescence overlay on white light (static) panel 1606 would give anatomical context during this procedure. If the dynamic panel 1608 is in white light mode, the user would scan the cavity or sample to find the location that corresponds to the static white light panel 1602, then use the fluorescence image overlaid on the white light image in panel 1606 to determine where the tumor tissue is located.

Figure 17:
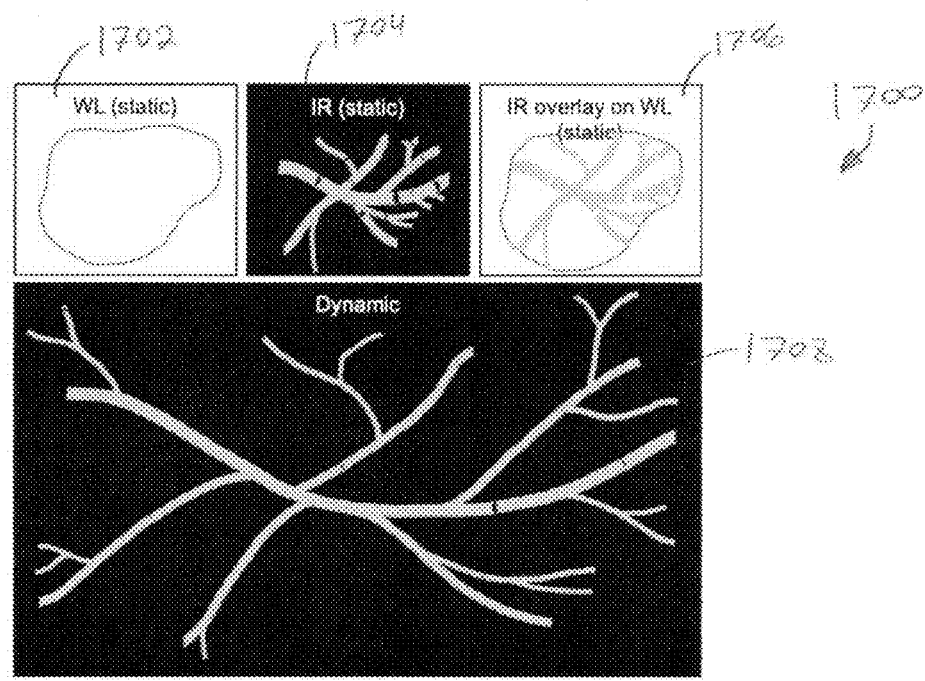

Referring now to FIG. 17, a similar arrangement can be provided with white light and infrared imagery. For example, a display 1700 can be divided into panels 1702, 1704, 1706, and 1708. Panel 1702 displays a static, white light image. Panel 1704 displays a static infrared image. Panel 1706 provides a static image of the infrared imagery overlaid on the white light image. Finally, panel 1708 provides a dynamic view that can be switched between white light and infrared imagery as desired.

If the dynamic panel 1708 is in infrared mode, then the user would scan the cavity/sample to match the infrared (static) panel 1704. The infrared overlay on white light (static) panel 1706 would give anatomical context during this procedure.

Figure 18:
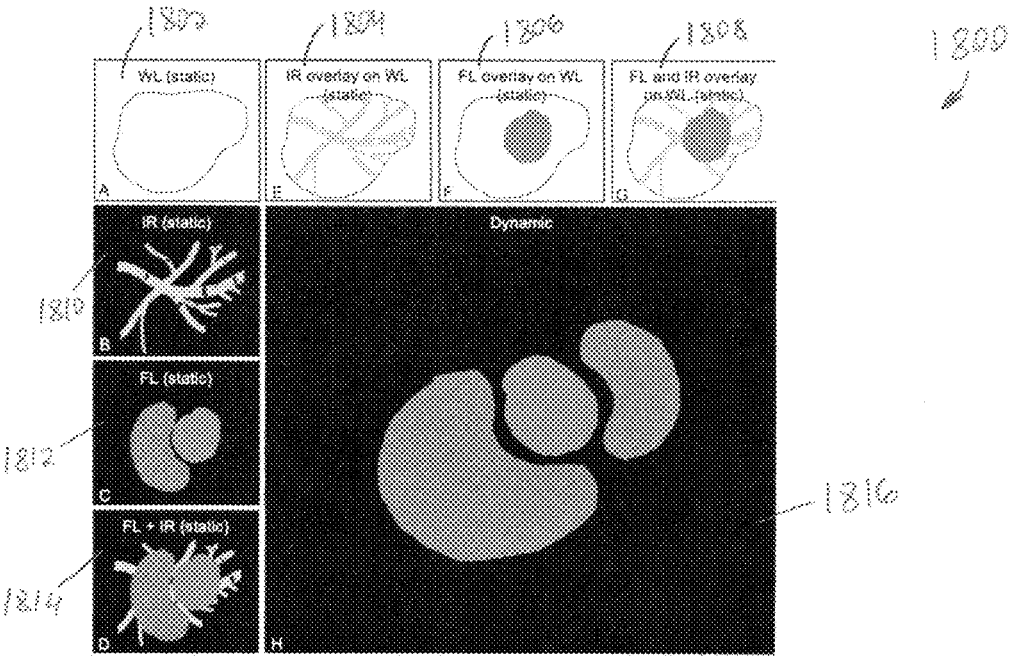

If the dynamic panel 1708 is in white light mode, then the user would scan the cavity/sample to find the location which corresponds to the white light (static) panel 1702, then use the infrared overlay on white light (static) panel 1706 to determine where relevant tissue is located Referring now to FIG. 18, another imaging mode is disclosed. A white light image, an infrared image, and, after switching the white light/infrared filter to the fluorescence filter, a fluorescence image, are captured in sequence. A display 1800 is partitioned into display panels 1802-1816 including white light, infrared, and fluorescence static panels and various overlays as indicated in FIG. 1800. A dynamic panel 1816 can display any one of white light images, infrared images, and fluorescence images. If the dynamic panel 1816 is in fluorescence mode, then the user would scan the cavity/sample to find the red fluorescence, and possibly tag the tissue with a vascular clip or similar. The fluorescence overlay on white light (static) panel would give anatomical context during this procedure. The fluorescence+ infrared (static) panel would show vasculature or other infrared fluorescence tissue components in this field of view, colocalized with green and red fluorescence. If the dynamic panel 1816 is in white light mode, then the user would scan the cavity/sample to find the location which corresponds to the white light (static) panel, then use the fluorescence overlay on white light (static) and infrared overlay on white light (static) panels to determine where relevant tissues are located.

With reference now to FIGS. 22-28, another embodiment of a handheld device 2200 is shown. While the embodiments discussed above describe various arrangements of switchable filters, such as the filter wheel 938 (FIG. 9), other embodiments, such as the embodiment illustrated in FIGS. 22-28, include multiple filters and multiple cameras having fixed positions. In such an embodiment, the handheld device 2200 can switch modes simply by activating different light sources and cameras, with no mechanical configuration changes being needed to move between modes.

Figure 22:
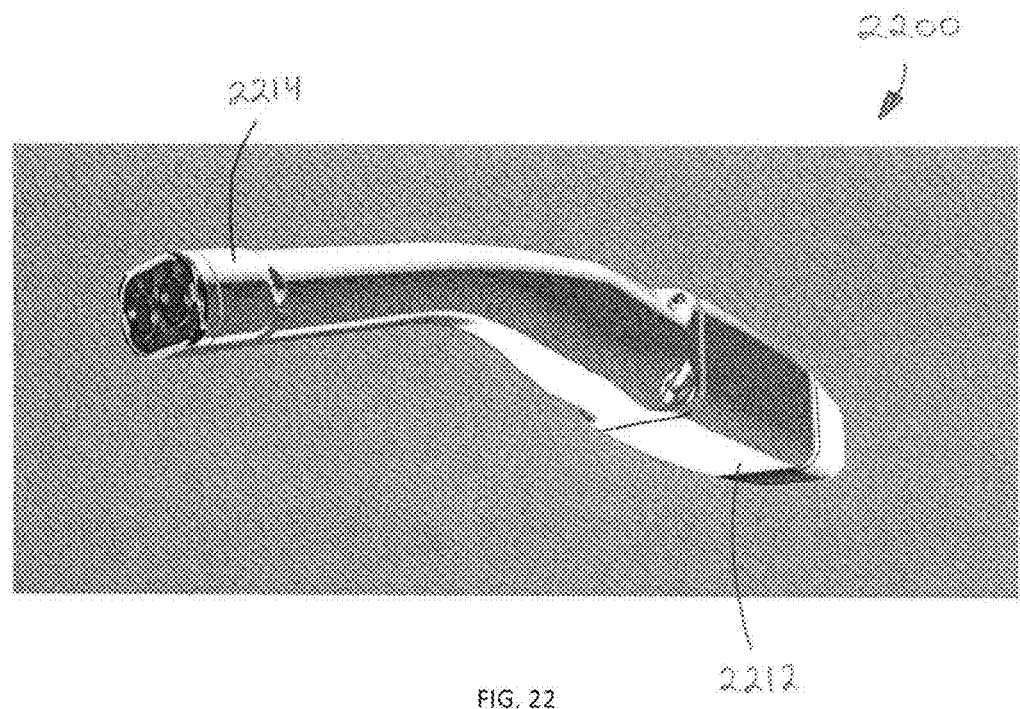
FIG. 22 is a perspective view of another embodiment of a handheld imaging device according to the present disclosure.

FIG. 22 shows a front perspective view of the handheld device 2200. The handheld device 2200 includes a first end portion 2212 that is sized and shaped for a user to grip and hold the handheld device 2200. Opposite the first end portion 2212 is a second end portion 2214 that can include one or more optical filters, one or more light sources, and one or more sensors such as imaging sensors, temperature sensors, and proximity sensors as in the embodiments discussed above.

Figure 23:
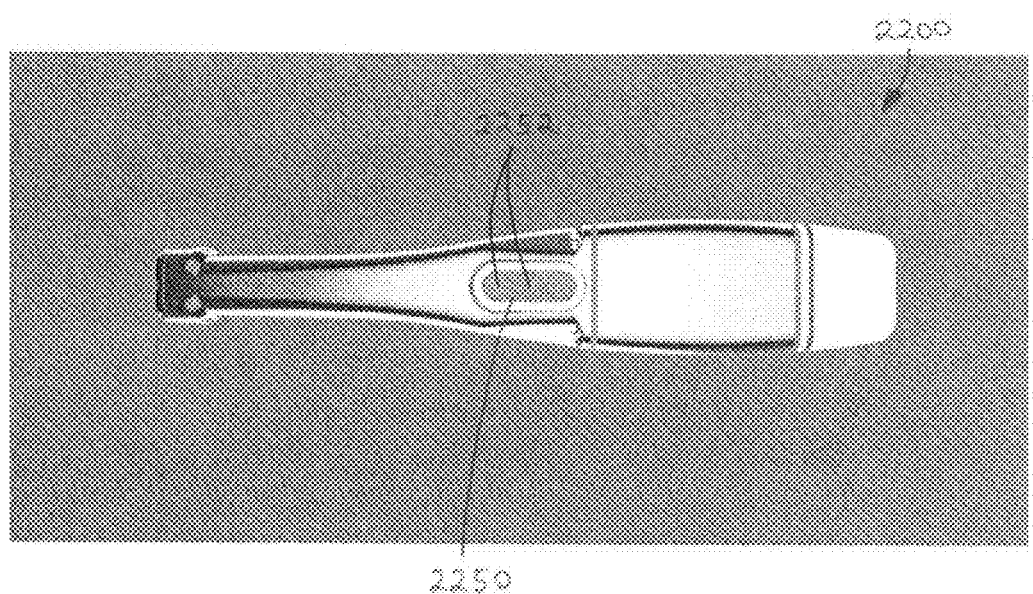
FIG. 23 is a top view of the handheld imaging device of FIG. 22.

Referring now to FIG. 23, a top view of the handheld device 2200 is shown. The handheld device 2200 includes a control array 2250. In the illustrated embodiment, the control array 2250 includes three buttons 2252. The buttons 2252 provide a user with an interface for switching between various imaging modes of the handheld device 2200, such as the various infrared imaging modes and fluorescence imaging modes discussed above in connection with other embodiments of the handheld device. The buttons 2252 can be hermetically sealed around a housing of the handheld device 2200 to simplify cleaning of the device and prevent contamination of internal components of the handheld device 2200.

Figure 24:
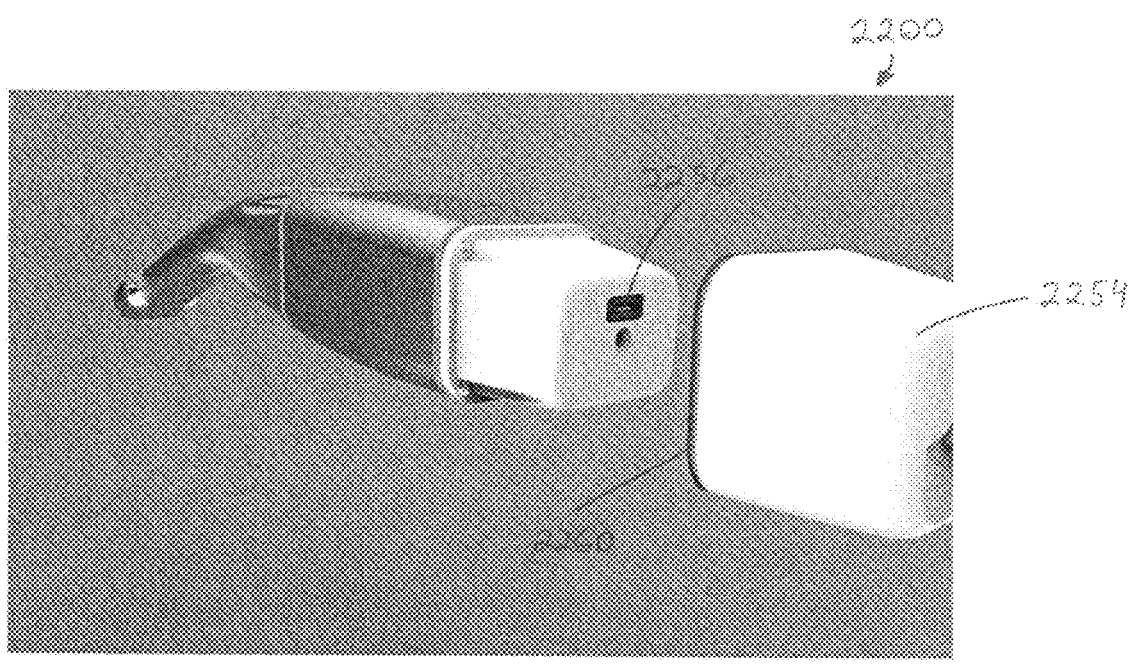
FIG. 24 is another perspective view of the handheld imaging device of FIG. 22 in a partly disassembled state.

Referring now to FIG. 24, a perspective view of the first portion 2212 of the handheld device 2200 is shown. In the embodiment of FIGS. 22-28, the handheld device 2200 has a removable cover portion 2254 that covers various components of the handheld device 2200, such as an electrical connection port 2256. In this illustrated embodiment, the electrical connection port 2256 is a universal serial bus (USB) port that facilitates connection of the handheld device 2200 to an external device, such as a computer (such as a PC workstation), a tablet, a phone or other device for various tasks such as updating software or firmware on the handheld device 2200, downloading images saved on memory of the handheld device 2200, etc. Additionally or alternatively, the device can be directly connected to a storage device, such as a USB stick, USB flash drive or thumb drive, to directly transfer data. For example, the handheld device can download data, images, and/or other material to the storage device. In another example, the storage device can be used to load new software or instructions onto the handheld device. As discussed above with respect to previous embodiments, such actions can optionally be accomplished with a wireless communication link between the handheld device

2200 and an external device such as computer, tablet, phone or other device. In some embodiments, the handheld device 2200 can include both a USB connection and wireless communication (such as Wi-Fi, Bluetooth, etc.) functionality.

Figure 25:
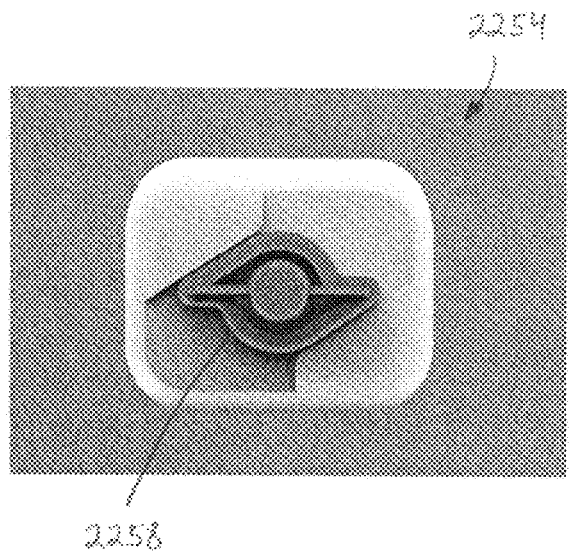
FIG. 25 is an end view of a cover portion of the handheld imaging device of FIG. 22.

FIG. 25 shows a rear view of the cover portion 2254 of the handheld device 2200. The cover portion 2254 includes a fastener device 2258 that facilitates removal and installation of the cover portion 2254 by the user. For example, in the embodiment of FIG. 25, the fastener device 2258 is a quarter-turn fastener that locks the cover portion 2254 in place on the handheld device 2200. To remove the cover portion 2254, the user simply rotates the fastener device 2258 one quarter turn and removes the cover portion 2254 from the handheld device 2258. The fastener device 2258 may take many other forms, as will be understood by those of ordinary skill in the art. The cover portion 2254 can also include a gasket 2260 (FIG. 24) that forms a seal between the cover portion 2254 and the handheld device 2200 to prevent contamination of the internal components of the handheld device 2200.

Figure 26:
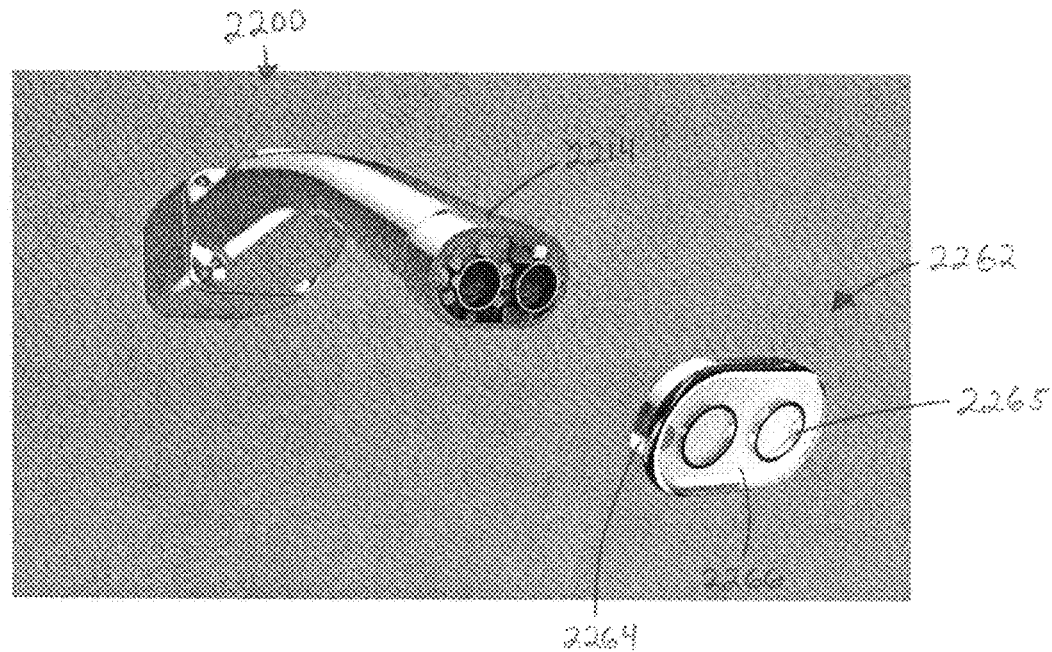
FIG. 26 is partly disassembled view of a distal end portion of the handheld imaging device of FIG. 22.

In some embodiments, the handheld device 2200 can include a removable lens assembly configured to protect components located in the second end 2214. Referring now to FIG. 26, the second end portion 2214 is shown with a lens assembly 2262 removed from the handheld device 2200. The lens assembly 2262 can comprise a lens frame 2264 bonded to a translucent lens 2266. In this embodiment, the lens frame 2264 can comprise a metal or metal alloy material, and the translucent lens 2266 can comprise glass or another translucent material, such as acrylic or other polymer. The translucent lens 2266 can be bonded to the lens frame 2264 with a bonding agent, such as a biocompatible epoxy or other suitable bonding material. The lens assembly 2262 can be coupled to the handheld device 2200 in any appropriate manner, such as by screws or other fasteners. In the exemplary embodiment of FIG. 26, the lens assembly 2262 includes opaque barriers 2265 that are positioned and configured to isolate different portions of the lens assembly 2262. For example, the opaque barriers 2265 are configured to isolate optical sensors (such as the optical sensors discussed in connection with FIG. 28) from various light sources (such as light sources 2270, 2274, and 2276 discussed in connection with FIG. 28) positioned in the second end 2214 of the handheld device 2200.

Figure 27:
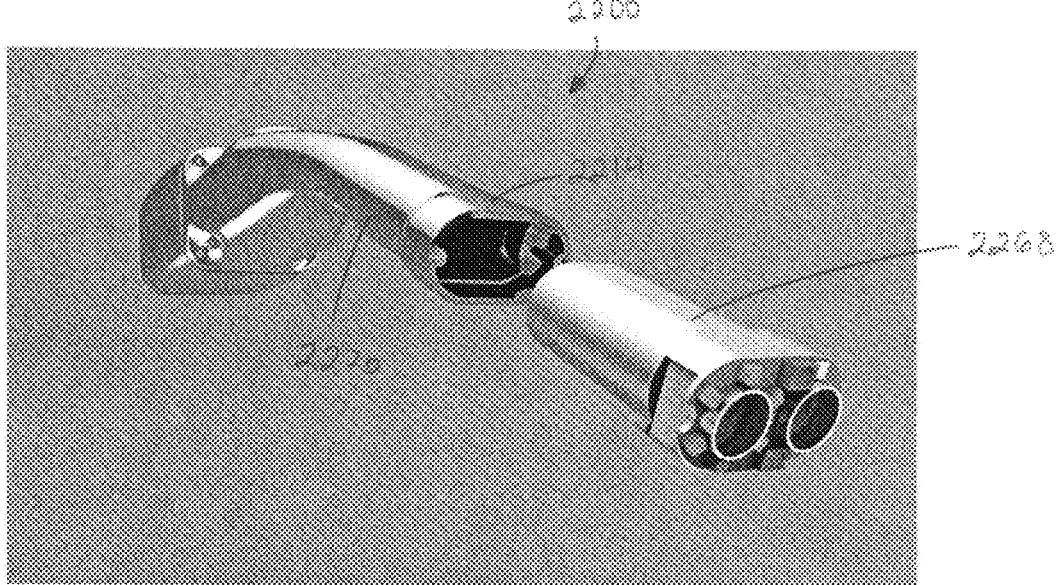
FIG. 27 is another partly disassembled view of the distal end portion of the handheld imaging device of FIG. 22.

FIG. 27 shows another disassembled view of the handheld device 2200. As shown in FIG. 27, the handheld device 2200 includes a heat sink 2268 in which the second end componentry, such as cameras, light sources, and various other sensors are contained as discussed below. The heat sink 2268 can be hollow to reduce weight while still providing effective heat transfer from the componentry in the second end 2214 up the body of the handheld device 2200. The heat sink 2268 may comprise a material having desired heat transfer characteristics, such as for example, copper, aluminum, other metals or metal alloys, or other heat conductive materials. When assembled in the handheld device 2200, the heat sink 2268 can extend through a neck portion 2270 of the handheld device from the second end 2214 toward the first end 2212 of the handheld device.

Figure 28:
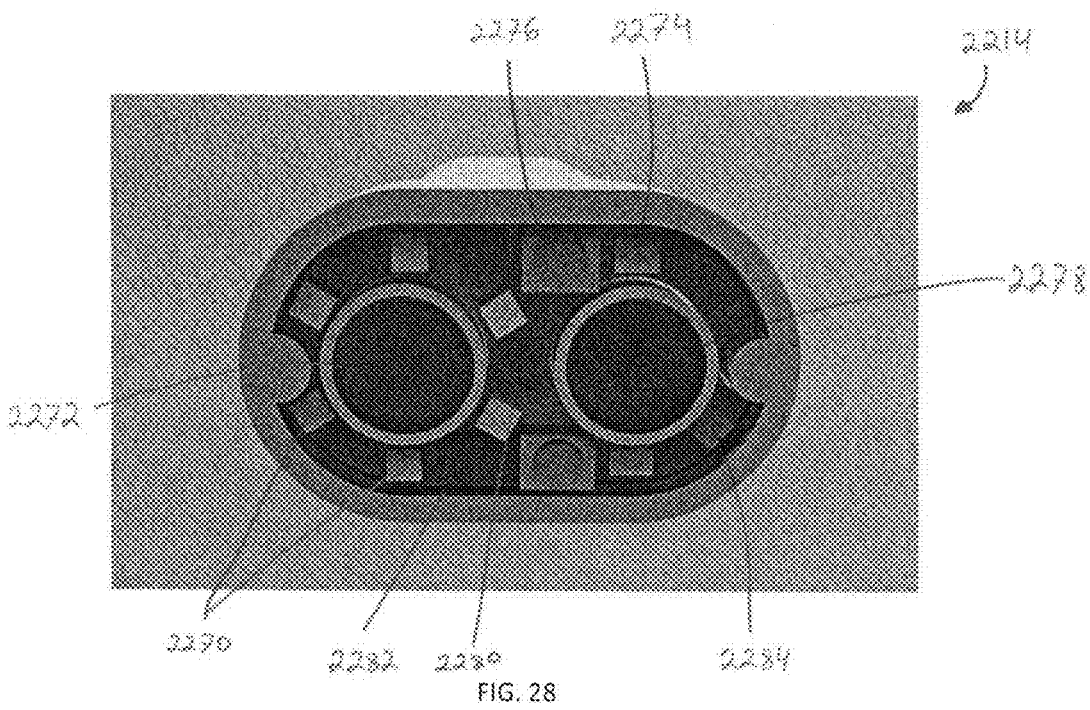
FIG. 28 is an end view of the distal end portion of the handheld imaging device of FIG. 22.

FIG. 28 is an enlarged view of the second end 2214 of the handheld device 2200 and shows various components in the second end 2214. The second end 2214 of the handheld device 2200 includes multiple excitation light sources 2270 (such as LEDs that emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof) and a first optical filter 2272 configured to support fluorescence imaging. In one example embodiment, the excitation light sources 2270 are configured to emit excitation light in the blue/violet range, for example, to emit excitation light having a wavelength of about 405 nm. The excitation light sources 2270 can be generally positioned around the first optical filter 2272, and a first optical sensor such as a camera (not visible) can be positioned behind the first optical filter 2272. FL imaging is used to visualize, for example, carcinoma in breast tissue. Carcinoma in breast tissue is visualized by illuminating breast tissue with violet light (405 nm) to excite protoporphyrin (PpIX) that has accumulated within cancerous cells following the ingestion of 5-aminolevulinic acid (ALA) by the patient. The localized PpIX within the cancerous tumors absorb the excitation light (405 nm) and then emits light at a longer wavelength (peak at 635 nm) allowing for the visualization of carcinoma in breast tissue. See, for example, FIGS. 12-15.

The second end 2214 also includes one or more white light sources 2274 (such as LEDs) that emit visible white light. The white light sources 2274 are located adjacent a second optical filter 2278. WL imaging illuminates the entire field of view (FOV) for viewing and capturing images of breast tissue under standard lighting conditions, similar to that present in an operating room setting.

Figure 29:
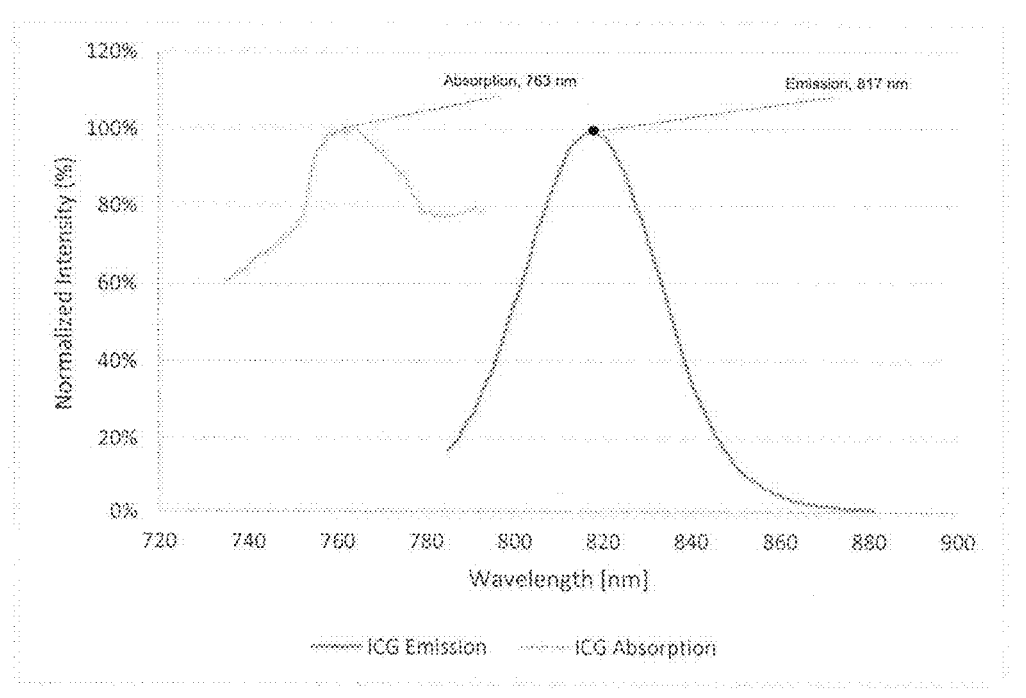
FIG. 29 is a chart showing ICG emission and ICG absorption wavelengths measured in a 60 uM aqueous solution.

One or more infrared light sources 2276 (infrared excitation light sources) are also located adjacent the second optical filter 2278. The infrared excitation light source(s) may emit an excitation light have a wavelength of between about 700 nm and about 1 mm. In one example embodiment, the infrared excitation light source(s) may emit an excitation wavelength of between about 750 nm and about 800 nm. In another example embodiment, the infrared excitation light source(s) may be configured to emit an excitation wavelength of between about 760 nm and 780 nm. In another example embodiment, the infrared excitation light source(s) may be configured to emit an excitation wavelength of about 760 nm±15 nm. The second optical filter 2278 can be positioned in front of a second optical sensor such as a camera (not shown) and the second optical filter 2278 can be configured to support imaging using white light or infrared light as discussed in detail above. IR imaging may be used with Indocyanine green (ICG) dye for visualizing biological structures such as lymph nodes or blood vessels during breast conserving surgery. ICG is a cyanine dye administered to patients intravenously, it binds tightly to β-lipoproteins and particularly albumins. Albumins are a family of globular proteins and they are commonly found in the blood plasma and the circulatory system. Additionally, because of the high protein content of lymph nodes, ICG accumulates in the lymphatic pathways and lymph nodes. The accumulation of ICG makes visualizing lymph nodes and vasculature using IR imaging possible. ICG is a dye which fluoresces after excitation under near-infrared light with a peak absorption at 800 nm and a peak emission at 835 nm. (See, for example, FIGS. 10 and 11.) As a further example, FIG. 29 shows ICG emission and ICG absorption wavelengths measured in a 60 uM aqueous solution.

The second end 2214 can include other components as well, such as an ambient light sensor 2280, a range finder 2282, a temperature sensor 2284, and other sensors or componentry. In exemplary embodiments, the handheld device 2200 includes a separate optical sensor (e.g., camera) positioned behind each of the first optical filter 2272 and the second optical filter 2278.

The control array 2250 (FIG. 23) can be operatively coupled to the various components in the handheld device 2200 though a controller (such as one or more microprocessors and associated components) to enable the user to switch between fluorescent, white light, or infrared imaging modes. The configuration of the handheld device 2200 of FIGS. 22-28 enables switching between fluorescence and IR/white light imaging modes without any mechanical configuration change in the handheld device 2200, thereby contributing to rapid changes in mode and potentially reducing the possibility for mechanical failure of components.

Furthermore, the devices and methods may include additional components or steps that were omitted from the drawings for clarity of illustration and/or operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present disclosure may be utilized independently, all as would be apparent to one skilled in the art after having the benefit of the description herein. Changes may be made in the elements described herein without departing from the spirit and scope of the present disclosure and following claims, including their equivalents.

It is to be understood that the particular examples and embodiments set forth herein are non-limiting, and modifications to structure, dimensions, materials, and methodologies may be made without departing from the scope of the present disclosure.

Furthermore, this description's terminology is not intended to limit the present disclosure. For example, spatially relative terms—such as "beneath," "below," "lower," "above," "upper," "bottom," "right," "left," "proximal," "distal," "front," and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the drawings.

For the purposes of this specification and appended claims, unless otherwise indicated, all numbers expressing quantities, percentages or proportions, and other numerical values used in the specification and claims, are to be understood as being modified in all instances by the term "about" if they are not already. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It should be understood that while the present disclosure has been described in detail with respect to various exemplary embodiments thereof, it should not be considered limited to such, as numerous modifications are possible without departing from the broad scope of the appended claims, including the equivalents they encompass.

We claim:

1. An imaging device, comprising:
a body having a first end portion configured to be held in a user's hand and a second end portion configured to direct light onto a surgical margin;
at least one excitation light source configured to excite autofluorescence emissions of tissue cells and fluorescence emissions of induced porphyrins in tissue cells of the surgical margin;
a white light source configured to illuminate the surgical margin during white light imaging of the surgical margin;
an imaging sensor;
a first optical filter configured to filter optical signals emitted by the surgical margin responsive to illumination with excitation light and permit passage of autofluorescence emissions of tissue cells and fluorescence emissions of the induced porphyrins in tissue cells to the imaging sensor; and
a second optical filter configured to filter optical signals emitted by the surgical margin responsive to illumination with white light and permit passage of white light emissions of tissues in the surgical margin to the imaging sensor, and
wherein the imaging sensor, the first optical filter, and the second optical filter are located at a distal end portion of the body of the imaging device.

2. The imaging device of claim 1, wherein the first optical filter and the second optical filter are configured to be alternatingly positioned to filter optical signals passing through the filter to the imaging sensor.

3. The imaging device of claim 2, wherein the first optical filter and the second optical filter are positioned on a filter wheel rotatable relative to the imaging sensor.

4. The imaging device of claim 3, wherein the filter wheel is operably coupled with an electric motor drive configured to rotate the filter wheel between a first position in which the first optical filter filters optical signals passing through the first optical filter to the imaging sensor and a second position in which the second optical filter filters optical signals passing through the second optical filter to the imaging sensor.

5. The imaging device of claim 4, wherein the device further comprises a processor, and the electric motor drive is in signal communication with the processor.

6. The imaging device of claim 3, wherein the rotatable filter wheel is positioned distally of the imaging sensor.

7. The imaging device of claim 1, wherein the excitation light source comprises a first excitation light source and a second excitation light source.

8. The imaging device of claim 7, wherein the first excitation light source is configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

9. The imaging device of claim 8, wherein the first excitation light source is configured to emit excitation light having a wavelength of about 400 nm to about 450 nm.

10. The imaging device of claim 9, wherein the first excitation light source is configured to emit excitation light having a wavelength of about 405 nm±10 nm.

11. The imaging device of claim 7, wherein the second excitation light source is configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

12. The imaging device of claim 11, wherein the second excitation light source is configured to emit excitation light having a wavelength of about 750 nm-800 nm.

13. The imaging device of claim 12, wherein the second excitation light source is configured to emit excitation light having a wavelength of between about 760 nm and about 780 nm.

14. The imaging device of claim 13, wherein the second excitation light source is configured to emit excitation light having a wavelength of about 760 nm±10 nm, a wavelength of about 770 nm±10 nm, or about 780 nm±10 nm.

15. The imaging device of claim 1, wherein the first optical filter is configured to permit passage of optical signals having a wavelength of about 500 nm to about 550 nm and/or about 600 nm to about 675 nm.

16. The imaging device of claim 1, wherein the first optical filter is configured to permit passage of optical signals having a wavelength of about 500 nm to about 550 nm and/or about 600 nm to about 725 nm.

17. The imaging device of claim 1, wherein the first optical filter is configured to permit passage of optical signals having a wavelength of about 635 nm.

18. The imaging device of claim 15, wherein the first optical filter is configured to attenuate passage of optical signals having a wavelength of about 500 nm to about 550 nm by an amount ranging from about 10% and about 90%.

19. The imaging device of claim 1, wherein the second optical filter is configured to permit passage of optical signals having a wavelength of below about 675 nm and above about 825 nm.

20. The imaging device of claim 1, wherein the second optical filter is configured to permit passage of optical signals having a wavelength below about 690 nm and above about 840 nm.

21. The imaging device of claim 19, wherein the second optical filter is configured to permit passage of optical signals having a wavelength of about 835 nm.

22. The imaging device of claim 1, wherein the imaging sensor comprises a complementary metal-oxide-semiconductor (CMOS) sensor.

23. The imaging device of claim 1, wherein the first optical filter and the second optical filter are each in a fixed position relative to the body of the imaging device.

24. An imaging device, comprising:

a body having a first end portion configured to be held in a user's hand and a second end portion configured to direct light onto a surgical margin;

at least one excitation light source configured to excite autofluorescence emissions of tissue cells and fluorescence emissions of induced porphyrins in tissue cells of the surgical margin;

a white light source configured to illuminate the surgical margin during white light imaging of the surgical margin;

an imaging sensor;

a first optical filter configured to filter optical signals emitted by the surgical margin responsive to illumination with excitation light and permit passage of autofluorescence emissions of tissue cells and fluorescence emissions of the induced porphyrins in tissue cells to the imaging sensor; and a second optical filter configured to filter optical signals emitted by the surgical margin responsive to illumination with white light and permit passage of white light emissions of tissues in the surgical margin to the imaging sensor, wherein the excitation light source is adjacent the first optical filter and the white light source is adjacent the second optical filter.

25. The imaging device of claim 23, wherein the imaging sensor is a first imaging sensor and the imaging device comprises a second imaging sensor, wherein the first optical filter is positioned to filter optical signals entering the first imaging sensor, and wherein the second optical filter is positioned to filter optical signals entering the second imaging sensor.

26. The imaging device of claim 1, further comprising a connection port configured to receive a connection cable for connecting the imaging device to an external computer system.

27. The imaging device of claim 26, wherein the connection port comprises features configured to interact with the connection cable to prevent rotation of the connection cable relative to the connection port.

28. An imaging system, comprising:

the imaging device of any one of claim 1; and a sterile drape configured to form a sterile barrier between the imaging device and an environment in which the imaging device is used.

29. The imaging system of claim 28, wherein the sterile drape comprises a first portion configured to form a sterile barrier between the imaging device and the environment in which the imaging device is used and a second portion configured to shield a surgical cavity from ambient light.

30. The imaging system of claim 28, wherein the sterile drape comprises an optically transparent lens cap positioned over the imaging sensor when the sterile drape is installed on the imaging device.

31. The imaging system of claim 30, wherein the lens cap is configured to engage a feature on the second end portion of the device.

32. The imaging system of claim 31, wherein the feature on the second end portion of the device comprises a circumferential groove.

33. The imaging system of claim 28, further comprising a darkening drape configured to reduce ambient light at a surgical margin to be imaged.

34. The imaging system of claim 28, further comprising a connection cable having a portion configured to connect to the connection port of the imaging device in a non-rotatable manner.

35. The imaging system of claim 34, further comprising a sterile sheath for the connection cable.

36. An imaging device, comprising:

a body having a first end portion configured to be held in a user's hand and a second end portion configured to direct light onto a surgical margin;

a first excitation light source configured to emit excitation light having a first wavelength;

a second excitation light source configured to emit excitation light having a second wavelength;

an imaging sensor configured to detect emissions of the surgical margin;

a first optical filter configured to filter optical signals emitted by the surgical margin responsive to illumination of the surgical margin with the first excitation light, the first optical filter configured to permit optical signals having a wavelength corresponding to a first characteristic of the surgical margin to pass through the first optical filter to the imaging sensor; and a second optical filter configured to filter optical signals emitted by the surgical margin responsive to illumination of the surgical margin with the first excitation light, the second optical filter configured to permit optical signals having a wavelength corresponding to a second characteristic of the surgical margin, different from the first characteristic, to pass through the second optical filter to the imaging sensor, and a lens element, wherein the lens element, the imaging sensor, the first optical filter, and the second optical filter are located at a distal end portion of the body of the imaging device, and wherein the lens element directly covers the imaging sensor, the first optical filter, and the second optical filter at the second end portion of the body of the imaging device.

37. The imaging device of claim 36, wherein the first optical filter is configured to be positioned to filter optical sensors passing to the image sensor when the first light source is actuated, and the second optical filter is configured to be positioned to filter optical sensors passing to the imaging sensor when the second light source is actuated.

38. The imaging device of claim 37, wherein the first and second optical filters are on a filter wheel rotatable relative to the imaging sensor.

39. The imaging device of claim 36, wherein in a first mode of operation, the first light source is actuated to illuminate a target tissue and the first optical filter is positioned to filter optical signals emitted by the target tissue in response to the illumination and entering the image sensor, and in a second mode of operation, the second light source is activated to illuminate the target tissue and the second optical filter is positioned to filter light entering the image sensor.

40. The imaging device of claim 36, wherein the first optical filter and the second optical filter are each in a fixed position relative to the body of the imaging device.

41. The imaging device of claim 40, wherein the first excitation light source is adjacent the first optical filter and the second excitation light source is adjacent the second optical filter.

42. The imaging device of claim 36, wherein the imaging sensor is a first imaging sensor and the imaging device comprises a second imaging sensor, wherein the first optical filter is positioned to filter optical signals entering the first imaging sensor, and wherein the second optical filter is positioned to filter optical signals entering the second imaging sensor.

43. An imaging system, comprising:
    the imaging device of claim 36; and
    a sterile drape configured to form a sterile barrier between the imaging device and an environment in which the imaging device is used.

44. The imaging system of claim 43, wherein the sterile drape comprises an optically transparent lens cap positioned over the imaging sensor when the sterile drape is installed on the imaging device.

45. The imaging system of claim 43, further comprising a darkening drape configured to reduce ambient light at a surgical cavity to be imaged.

46. The imaging system of claim 43, further comprising a connection cable having a portion configured to connect to a connection port of the imaging device in a non-rotatable manner.

47. The imaging system of claim 46, further comprising a sterile sheath for the connection cable.

48. A method of imaging tissue at a surgical margin or a surgical cavity, comprising:
    illuminating the tissue at the surgical margin or the surgical cavity with a first excitation light source configured to emit excitation light having a first wavelength;
    receiving optical signals emitted by the tissue at the surgical margin or the surgical cavity through a first optical filter in an imaging device;
    illuminating the tissue at the surgical margin or the surgical cavity with a second excitation light source configured to emit excitation light having a second wavelength; and
    receiving optical signals emitted by the tissue at the surgical margin or the surgical cavity through a second optical filter in the imaging device,
    wherein the first excitation light source is adjacent the first optical filter and the second excitation light source is adjacent the second optical filter.

49. The method of claim 48, further comprising:
    based on a signal from a processor:
        moving the first optical filter away from a position at which the optical signals emitted from the tissue at the surgical margin or the surgical cavity are filtered through the first optical filter; and
        moving the second optical filter to a position at which the optical signals emitted from the tissue at the surgical margin or the surgical cavity are filtered through the second optical filter.

50. The method of claim 48, wherein moving the first optical filter away from a position and moving the second optical filter to a position comprises actuating an electric motor to move the first optical filter and the second optical filter.

51. The method of claim 50, wherein actuating an electric motor to move the first optical filter and the second optical filter comprises actuating the electric motor to rotate a filter wheel comprising the first optical filter and the second optical filter.

52. The method of claim 48, wherein illuminating the tissue at the surgical margin or the surgical cavity with a first excitation light source configured to emit excitation light having a first wavelength comprises illuminating the tissue with a first excitation light source having a wavelength of about 405 nm±10 nm.

53. The method of claim 50, wherein illuminating the tissue at the surgical margin or the surgical cavity with a second excitation light source configured to emit excitation light having a second wavelength comprises illuminating the tissue with a second excitation light source having a wavelength of about 750 nm-800 nm.

54. The method of claim 50, wherein receiving optical signals emitted by the tissue at the surgical margin or the surgical cavity through the first optical filter comprises filtering optical signals emitted by the tissue through a filter that permits passage of optical signals having a wavelength of about 500 nm to about 550 nm and/or about 600 nm to about 675 nm.

55. The method of claim 50, wherein receiving optical signals emitted by the tissue at the surgical margin or the surgical cavity through a first optical filter comprises filtering optical signals emitted by the tissue through a filter that permits passage of optical signals having a wavelength of about 500 nm to about 550 nm and/or about 600 nm to about 725 nm.

56. The method of claim 50, wherein receiving optical signals emitted by the tissue at the surgical margin or the surgical cavity through a second optical filter comprises filtering optical signals emitted by the tissue through a filter that permits passage of optical signals having a wavelength of below about 675 nm and above about 825 nm.

57. The method of claim 50, wherein receiving optical signals emitted by the tissue at the surgical margin or the surgical cavity through a second optical filter comprises filtering optical signals emitted by the tissue through a filter that permits passage of optical signals having a wavelength below about 690 nm and above about 840 nm.

58. The method of claim 50, further comprising administering aminolevulinic acid (ALA) to a patient prior to illuminating tissue at the surgical margin or the surgical cavity.

59. The method of claim 50, further comprising administering at least one of IRDye 800, Indocyanine green (ICG), or another infrared dye to a patient prior to illuminating tissue at the surgical margin or the surgical cavity.

60. The method of claim 50, further comprising positioning a sterile drape on the imaging device prior to illuminating tissue at the surgical margin or the surgical cavity.

61. The method of claim 50, further comprising reducing ambient light at a surgical site in which the surgical margin or the surgical cavity is located.

62. The method of claim 61, wherein reducing ambient light comprises, prior to illuminating tissue at the surgical margin or the surgical cavity, positioning a darkening drape around the surgical site such that the surgical margin or the surgical cavity is positioned within a field of view of the imaging device in an interior of the darkening drape.

63. The method of claim 50, further comprising determining whether a level of ambient light is sufficient to permit fluorescence imaging.

64. A method of visualizing breast cancer cells, comprising:
    administering one or more imaging agents to a patient, wherein at least one of the imaging agents is configured to induce formation of at least one protoporphyrin in breast cancer cells;

subsequent to administration of the one or more imaging
agents, illuminating breast tissue of the patient with a
first excitation light source configured to cause proto-
porphyrin to fluoresce;

receiving, by an imaging sensor, optical signals respon-
sive to illumination with the first excitation light and
emitted by cells within the breast tissue containing
protoporphyrin through a first optical filter in an imag-
ing device;

illuminating the breast tissue with a white light source;
and receiving, by the imaging sensor, optical signals respon-
sive to illumination with the white light and emitted by
the breast tissue through a second optical filter in the
imaging device, wherein the imaging sensor, the first optical filter, and the
second optical filter are located at a distal end portion
of a body of the imaging device.

65. The method of claim 64, wherein administering one or
more agents to a patient comprises administering aminole-
vulinic acid (ALA) to the patient.

66. The method of claim 64, wherein administering one or
more agent to a patient comprises administering at least one
of IRDye 800 and Indocyanine green (ICG) to the patient.

67. The method of claim 64, wherein receiving optical
signals responsive to illumination with the first excitation
light and emitted by cells within the breast tissue containing
protoporphyrin through a first optical filter comprises receiv-
ing optical signals through the first optical filter at a first
imaging sensor.

68. The method of claim 67, wherein receiving optical
signals responsive to illumination with the white light and
emitted by the breast tissue through a second optical filter
comprises receiving optical signals through the second opti-
cal filter at a second imaging sensor.

69. The method of claim 64, further comprising moving
the first optical filter from a first position at which the optical
signals are filtered by the first optical filter prior to being
received at an imaging device, and moving the second
optical filter to the first position.

70. The method of claim 64, further comprising operably
coupling the imaging device to an external computer system
by a cable connected to a port of the imaging device.

71. The method of claim 64, further comprising position-
ing a sterile drape on the imaging device prior to illuminat-
ing breast tissue of the patient.

72. The method of claim 64, further comprising reducing
ambient light at a surgical site at which the breast tissue is
located.

73. The method of claim 72, wherein reducing ambient
light comprises, prior to illuminating breast tissue, position-
ing a darkening drape around the surgical site such that the
breast tissue is positioned within a field of view of the
imaging device in an interior of the darkening drape.

74. The method of claim 64, further comprising deter-
mining whether a level of ambient light is sufficient to
permit fluorescence imaging.

75. A portable, handheld imaging device, comprising:
a body portion having a first end portion configured to be
held in a user's hand and a second end portion config-
ured to direct light into a surgical margin, the second
end portion having a distal tip comprising:
at least one excitation light source configured to excite
autofluorescence emissions of tissue cells and fluores-
cence emissions of induced porphyrins in tissue cells of
the surgical margin, a white light source configured to illuminate the surgical
margin during white light imaging of the surgical
margin,
an infrared light source,
a first imaging sensor configured to support a first imaging
mode,
a first optical filter configured to filter optical signals
emitted by the surgical margin responsive to illumina-
tion with excitation light and permit passage of auto-
fluorescence emissions of tissue cells and fluorescence
emissions of the induced porphyrins in tissue cells to
the first imaging device,
a second imaging sensor configured to support a second
imaging mode, and
a second optical filter configured to filter optical signals
emitted by the surgical margin responsive to illumina-
tion with white light and permit passage of white light
emissions of tissues in the surgical margin to the second
imaging device,
wherein the first imaging sensor, the first optical filter, the
second imaging sensor, and the second optical filter are
located at a distal end portion of the body of the
imaging device.

76. The imaging device of claim 75, wherein the distal tip
further comprises an ambient light sensor.

77. The imaging device of claim 75, wherein the distal tip
further comprises a range finder.

78. The imaging device of claim 75, wherein the first
imaging mode is a fluorescent imaging mode and the second
imaging mode is a white light imaging mode.

79. The imaging device of claim 75, wherein the first end
portion includes a plurality of controls configured to actuate
the imaging device, toggle between the at least one excita-
tion light source and the white light source, control the at
least one excitation light source and/or the white light
source, and/or switch between the first imaging mode and
the second imaging mode.

80. The imaging device of claim 79, wherein the plurality
of controls include at least one button, switch, and/or
capacitive discharge sensors.

81. The imaging device of claim 75, wherein the body
portion has a generally elongated shape.

82. The imaging device of any claim 75, further compris-
ing a wireless module configured to perform wireless com-
munication with an external device.

83. The imaging device of claim 82, wherein the wireless
module is configured to communicate using Wi-Fi and/or
Bluetooth).

84. The imaging device of claim 75, wherein the at least
one excitation light source comprises a first excitation light
source and a second excitation light source.

85. The imaging device of claim 84, wherein the first
excitation light source is configured to emit excitation light
having a wavelength of about 350 nm-about 400 nm, about
400 nm-about 450 nm, about 450 nm-about 500 nm, about
500 nm-about 550 nm, about 550 nm-about 600 nm, about
600 nm-about 650 nm, about 650 nm-about 700 nm, about
700 nm-about 750 nm, about 750 nm-about 800 nm, about
800 nm-about 850 nm, about 850 nm-about 900 nm, and/or
combinations thereof.

86. The imaging device of claim 85, wherein the first
excitation light source is configured to emit excitation light
having a wavelength of about 400 nm to about 450 nm.

87. The imaging device of claim 86, wherein the first
excitation light source is configured to emit excitation light
having a wavelength of about 405 nm±10 nm.

88. The imaging device of claim 84, wherein the second excitation light source is configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

89. The imaging device of claim 88, wherein the second excitation light source is configured to emit excitation light having a wavelength of about 750 nm-800 nm.

90. The imaging device of claim 89, wherein the second excitation light source is configured to emit excitation light having a wavelength of about 760 nm±10 nm, about 770 nm±10 nm, or about 780 nm±10 nm.

91. The imaging device of claim 75, wherein the first imaging sensor and the second imaging sensor respectively comprise a complementary metal-oxide-semiconductor (CMOS) sensor.

92. An imaging system, comprising:
the imaging device of any one of claim 75; and
a sterile drape configured to form a sterile barrier between the imaging device and an environment in which the imaging device is used.

93. The imaging system of claim 92, wherein the sterile drape comprises a first portion configured to form a sterile barrier between the imaging device and the environment in which the imaging device is used and a second portion configured to shield a surgical cavity from ambient light.

94. A portable, handheld imaging device, comprising:
a body having a first body portion configured to be held in a user's hand and a second body portion having a first end connected to the first body portion and a second free end extending from the body portion, a length of the second body portion extending between the first and second ends along a longitudinal axis of the second body portion, wherein the second free end forms an angle with respect to the longitudinal axis of the second body portion and is configured to direct light onto a surgical margin, the second free end comprising:
a first optical sensor positioned behind a first optical filter and a plurality of excitation light sources positioned around the first optical filter, the first optical filter being configured to filter optical signals emitted by the surgical margin responsive to illumination with excitation light emitted by the plurality of excitation light sources and to permit passage of autofluorescence emissions of tissue cells and fluorescence emissions of induced porphyrins in cancerous tissue cells to the first optical sensor, and
a second optical sensor positioned behind a second optical filter, one or more white light sources and one or more infrared light sources being positioned around the second optical filter, the second optical filter being configured to filter optical signals reflected by the surgical margin responsive to illumination with white light and to permit passage of the reflected white light from tissues in the surgical margin to the second optical filter, the second optical filter being positioned adjacent to the first optical filter;
a controller configured to switch the portable, handheld imaging device between a fluorescence imaging mode, a white light imaging mode, and an infrared imaging mode;
a processor configured to receive fluorescence data, white light data, and infrared data from the first and second optical sensors and further configured to output one or more images comprising one or more of fluorescence data, white light data, and infrared data.

95. The imaging device of claim 94, wherein the second free end further comprises one or more structures configured to isolate each of the first and the second optical sensors from each of the plurality of excitation light sources, the one or more white light sources, and the one or more infrared light sources.

\* \* \* \* \*